(12) United States Patent
Kuroda et al.

(10) Patent No.: US 7,652,768 B2
(45) Date of Patent: Jan. 26, 2010

(54) CHEMICAL SENSING APPARATUS AND CHEMICAL SENSING METHOD

(75) Inventors: Ryo Kuroda, Kawasaki (JP); Tomohiro Yamada, Yokohama (JP); Masaya Ogino, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 44 days.

(21) Appl. No.: 11/948,490

(22) Filed: Nov. 30, 2007

(65) Prior Publication Data

US 2008/0130003 A1    Jun. 5, 2008

(30) Foreign Application Priority Data

Dec. 1, 2006    (JP)    ............................. 2006-325949
Nov. 13, 2007    (JP)    ............................. 2007-294265

(51) Int. Cl.
*G01N 21/55* (2006.01)

(52) U.S. Cl. ...................................... 356/445

(58) Field of Classification Search ................. 356/432, 356/441, 445–448; 385/17, 12, 30; 372/96, 372/45.01–46.016, 26, 28, 38.01–38.02, 372/32; 422/82.05, 82.11
See application file for complete search history.

(56) References Cited

U.S. PATENT DOCUMENTS

| 6,093,536 A | 7/2000 | Drake et al. |
| 2003/0132392 A1 | 7/2003 | Kuroda et al. |
| 2003/0232257 A1 * | 12/2003 | Inao et al. ..................... 430/5 |
| 2006/0164654 A1 * | 7/2006 | Eah et al. ..................... 356/498 |
| 2006/0246438 A1 * | 11/2006 | McCall et al. .................. 435/6 |

FOREIGN PATENT DOCUMENTS

| DE | 19751706 A1 * | 6/1999 |
| WO | WO2006/030957 | * 3/2006 |

* cited by examiner

*Primary Examiner*—Tarifur Chowdhury
*Assistant Examiner*—Michael Lapage
(74) *Attorney, Agent, or Firm*—Fitzpatrick, Cella, Harper & Scinto

(57) ABSTRACT

In a chemical sensing apparatus utilizing a surface plasmon resonance in a small aperture formed in a metal thin film or on a surface of a metal fine particle, a capturing substance is disposed in the small aperture or on the surface of the metal fine particle for capturing a target substance. A marker substance, having a size comparable to that of the small aperture or the metal fine particle is combined with the target substance. As a result, a spectral change is increased in the transmitted light or the scattered light, induced by a surface plasmon resonance and resulting from the capture of the target substance.

16 Claims, 9 Drawing Sheets

CHEMICAL SENSING APPARATUS AND CHEMICAL SENSING METHOD

BACKGROUND OF THE INVENTION

1. Field of the Invention

The present invention relates to a chemical sensor, and more particularly to a surface plasmon resonance biosensor for detecting a biosubstance, adapted for use in medical diagnosis, health checkup and food inspection.

2. Description of the Related Art

In the fields of medical diagnosis and food inspection, utilization of biosensors for detecting various physiological substances and biosubstances is advancing in recent years. In particular, various biosensors capable of detecting physiological substances and biosubstances of a small amount contained in a sample are being developed. Also desired is the development of a compact low-cost biosensor, capable of a high-speed sensing.

Also being developed is a biosensor for use in the detection of an antigen molecule utilizing an antigen-antibody reaction, and in the detection of a ligand molecule utilizing coupling of a ligand molecule with a receptor protein. Also in a biosensor executing detection by forming a composite substance of a capturing molecule, which specifically captures a physiological substance or a biosubstance constituting the target of detection, and such detection target substance, it is desired to achieve compactification, sensing performed at a higher speed and a low cost. A biosensor utilizing surface plasmon resonance as a transducer is considered promising for accomplishing compactification and measuring the amount of formed composite member precisely and within a short time. Such a surface plasmon resonance (SPR) biosensor, for example an SPR biosensor of Kretschmann construction, utilizes a metal thin film formed on the surface of a prism in such an arrangement that an incident light angle satisfies a total-reflection condition. Thus, there is utilized a surface plasmon resonance absorption (scattering), resulting from a coupling of a surface plasmon that is generated on the surface of the metal thin film disposed on the surface of the prism in such total-reflection arrangement and of incident light. A substance is adsorbed on the surface of the metal thin film, and a peak wavelength of the light inducing the surface plasmon resonance adsorption (scattering), namely the surface plasmon resonance wavelength, is shifted. A phenomenon that the shift amount of the surface plasmon resonance wavelength increases with an increase in the amount of substance adsorbed on the surface of the metal thin film, is utilized to measure the amount of the substance adsorbed on the surface of the metal thin film.

On the other hand, for the purpose of sensing of a high sensitivity, US 2003/0132392 proposes a localized surface plasmon resonance sensor utilizing a small aperture formed in the metal thin film. Such localized surface plasmon resonance sensor adopts a construction of irradiating the small aperture, formed in the metal thin film on a substrate, with a light, and measuring the transmittance of the light transmitted by the small aperture, thereby detecting a change in the medium in the vicinity of the small aperture.

SUMMARY OF THE INVENTION

In the surface plasmon resonance (SPR) biosensor of Kretschmann type, the apparent increase in the shift amount of the surface plasmon resonance wavelength is dependent on the amount of the substance adsorbed on the surface of the metal thin film. On the other hand, in the case that the concentration of the detection target substance contained in the sample is low, the areal density of the detection target substance, adsorbed on the surface of the metal thin film, also becomes low. As a result, also decreased is a change in the detected light amount, that is dependent on the apparent shift amount of the surface plasmon resonance wavelength, and it becomes difficult to detect the concentration of the detection target substance with a high precision.

Also the aforementioned localized surface plasmon resonance sensor utilizes a wavelength shift in the light inducing a localized surface plasmon resonance absorption (scattering). Such localized surface plasmon resonance absorption (scattering) is derived from a localized surface plasmon that is present on the surface of the small aperture, formed in the metal thin film, particularly in a lateral wall of the small aperture. In the case that the concentration of the detection target substance contained in the sample is low, the areal density of the detection target substance, immobilized on the surface of the small aperture through an intermolecular bonding with the capturing molecule immobilized on the surface of the small aperture, also becomes low. As a result, also decreased is a change in the transmitted light amount, that is dependent on the apparent shift amount of the localized surface plasmon resonance wavelength, thus constituting a factor hindering a highly precise detection of the concentration of the detection target substance.

On the other hand, in case of use in a medical diagnosis in an early stage of a disease, it becomes necessary to detect a protein of an extremely small amount present in the specimen. Also in case of use in a food inspection, it becomes necessary to detect target bacteria with a high accuracy in a stage where the number of bacteria is very little. Thus, in order to measure the concentration of the detection target substance with high accuracy and precision even in the case that the detection target substance is present in a low concentration in the specimen, a higher sensitivity is desired for the biosensor to be employed for detecting such detection target substance. For example, there is desired the development of a biosensor of a detecting ability of "single molecule level", in which a molecule of the detection target biosubstance combines with plural capturing molecules immobilized with a predetermined areal density on the sensor surface.

The present invention is to solve the aforementioned problem, and an object thereof is to provide a chemical sensing apparatus capable, in the detection of a target substance to be immobilized through the bonding with the capturing molecule immobilized with a predetermined areal density on the sensor surface, of detection of high accuracy and precision even when the detection target substance is immobilized at a "single molecule level". Another object of the present invention is to provide a chemical sensing method capable, utilizing the chemical sensing apparatus, of detecting a detection target substance, contained with an extremely low concentration in the specimen, with high accuracy and precision.

The present invention utilizes a local surface plasmon resonance phenomenon of a local surface plasmon, induced by an irradiating light incident to a small aperture formed in a metal thin film or to a surface of a metal fine particle and caused by a coupling of a near-field light and a free electron of the metal. A target substance combined with a marker substance is immobilized, by a bonding with a capturing substance, at a distance shorter than ½ of wavelength to the small aperture. Otherwise, a target substance combined with a marker substance is immobilized, by a bonding with a capturing substance, to the surface of the metal fine particle. The target substance combined with the marker substance, immobilized at a distance shorter than ½ of wavelength, particularly the presence of the marker substance, causes a significant influence on an electron wave generated on the metal surface. Thus a significant change is induced in the resonance condition (resonance frequency) of the localized surface plasmon resonance. The present invention utilizes this phenomenon to achieve a significant improvement in the detection sensitivity.

The present invention is directed to a chemical sensing apparatus for detecting a target substance by immobilizing the target substance through a bond with a capturing substance, comprising: a light source; a metal thin film having an aperture smaller than a wavelength of a light emitted from the light source, or a metal fine particle smaller than the wavelength; a transparent substrate bearing the metal thin film or the metal fine particle on the surface of the transparent substrate; a capturing substance bonded to a metal surface of the metal thin film in the vicinity of the aperture or to a surface of the metal fine particle; a marker substance combined with a target substance having from $1/10$ times to 10 times of the dimension of the aperture or the metal fine particle and capable of bonding to the capturing substance; and a photodetector for detecting a transmitted light through the aperture or a scattered light emitted from the metal fine particle when irradiating the metal thin film or the metal fine particle with the light emitted from the light source, wherein the target substance combined with the marker substance is immobilized on the metal surface of the metal thin film in the vicinity of the aperture or on the surface of the metal fine particle through a bond with the capturing substance to detect the target substance by a change in the transmitted light or the scattered light.

In the chemical sensing apparatus, plural such apertures formed in the metal thin film or metal fine particles can be provided, and the plural apertures or the plural metal fine particles are arranged in a one-dimensional or two-dimensional away on the surface of the transparent substrate. The photodetector can have a function capable of detecting the transmitted light through the plural apertures or the scattered light emitted from the plural metal fine particles, arranged in the one-dimensional or two-dimensional array on the surface of the transparent substrate, as one-dimensional or two-dimensional image information.

In the chemical sensing apparatus, the marker substance can be a second metal fine particle.

In the chemical sensing apparatus, the marker substance can be a magnetic fine particle.

In the chemical sensing apparatus, the photodetector can have a function capable of detecting a spectral shape of the transmitted light through the aperture formed in the metal thin film, or the scattered light emitted from the metal fine particle.

In the chemical sensing apparatus, the aperture formed in the metal thin film or the metal fine particle can be provided in plural units, and the plural apertures or the plural metal fine particles are arranged in a one-dimensional or two-dimensional array on the surface of the transparent substrate. The photodetector can have a function capable of detecting the transmitted light through the plural apertures or the scattered light emitted from the plural metal fine particles, arranged in the one-dimensional or two-dimensional array on the surface of the transparent substrate, as one-dimensional or two-dimensional image information.

In the chemical sensing apparatus, the irradiating method of the light from the light source and the arrangement of the photodetector can be in an dark field illumination arrangement, in which, when the light from the light source irradiates the metal thin film having the aperture or the metal fine particle, the transmitted light through the aperture formed in the metal thin film or the scattered light from the metal fine particle alone is detected by the photodetector.

In the chemical sensing apparatus, the chemical sensing apparatus can be incorporated in a chemical microanalytical system, as a detection unit in a detection portion of the chemical microanalytical system.

In the chemical sensing apparatus, the chemical sensing apparatus can be incorporated in a target substance detecting system utilizing a DNA chip, as a detection unit in a detection portion of the target substance detecting system utilizing a DNA chip.

In the chemical sensing apparatus, the chemical sensing apparatus can be incorporated in a target substance detecting system utilizing a protein chip, as a detection unit in a detection portion of the target substance detecting system utilizing a protein chip.

The present invention is directed to a chemical sensing method for detecting a target substance by immobilization thereof by a bonding with a capturing substance, the method comprising use of an apparatus comprising: a light source; a metal thin film having an aperture smaller than a wavelength of a light emitted from the light source, or a metal fine particle smaller than the wavelength; a transparent substrate bearing the metal thin film or the metal fine particle on the surface of the transparent substrate; a capturing substance bonded to a metal surface of the metal thin film in the vicinity of the aperture or to a surface of the metal fine particle; a marker substance combined with a target substance having from $1/10$ times to 10 times of the dimension of the aperture or the metal fine particle and capable of bonding to the capturing substance; and a photodetector for detecting a transmitted light through the aperture or a scattered light emitted from the metal fine particle when irradiating the metal thin film or the metal fine particle with the light emitted from the light source, wherein the target substance combined with the marker substance is immobilized on the metal surface of the metal thin film in the vicinity of the aperture or on the surface of the metal fine particle through a bond with the capturing substance to detect the target substance by a change in the transmitted light or the scattered light; and the method comprising sensing operations of: immobilizing the target substance combined with the marker substance by the bonding to the capturing substance, on the metal surface of the metal thin film in the vicinity of the aperture or on the surface of the metal fine particle; when the immobilization is made, irradiating the metal thin film having the aperture or the metal fine particle by the light from the light source; and in a state under irradiation by the light from the light source, detecting the transmitted light transmitted by the aperture formed in the metal thin film or the scattered light emitted from the metal fine particle by the photodetector.

In the chemical sensing method, the photodetector can have a function capable of detecting a spectral shape of the transmitted light through the aperture formed in the metal thin film, or the scattered light emitted from the metal fine particle, and in detecting the transmitted light transmitted by the aperture formed in the metal thin film or the scattered light emitted from the metal fine particle by the photodetector, can detect a spectral shape of the transmitted light through the aperture formed in the metal thin film, or the scattered light emitted from the metal fine particle.

In the chemical sensing method, the photodetector can have a function of detecting the light from a one-dimensionally or two-dimensionally spreading measurement area, as one-dimensional or two-dimensional image information, and in detecting the transmitted light through the aperture formed in the metal thin film or the scattered light from the metal fine particle, can detect the light from an area irradiated with the light from the light source, as one-dimensional or two-dimensional image information.

In the chemical sensing method can comprise detecting the transmitted light through the aperture formed in the metal thin film or the scattered light from the metal fine particle by the photodetector, an operation of calculating a gradation of a light intensity, based on the result of measurement of the light intensity detected by the photodetector.

In the chemical sensing method, the capturing substance, bonded to the metal surface of the metal thin film in the vicinity of the aperture or to the surface of the metal fine particle, can be bonded to the metal surface by irradiating the metal surface of the metal thin film in the vicinity of the aperture or the surface of the metal fine particle with a second light to induce a photochemical reaction that is used for bonding the capturing substance to the metal surface.

In the chemical sensing apparatus and the chemical sensing method of the present invention, a capturing substance bonded to the vicinity of a small aperture formed in a metal thin film or to a metal fine particle, is bonded to a target substance combined with a marker substance of a size comparable to the aperture or the metal fine particle. The bonding of the target substance combined with the marker substance of a size comparable to the aperture or the metal fine particle increases the shift amount of the observed peak wavelength of the localized surface plasmon resonance. Therefore, in the detection utilizing the localized surface plasmon resonance, the sensitivity of detection of the target substance can be made to a single molecular level. Such high detection sensitivity enables to advantageously utilize the chemical sensing apparatus and the chemical sensing method of the present invention to the medical diagnosis in an early stage of the disease and to the detection of bacteria of very few number.

Further features of the present invention will become apparent from the following description of exemplary embodiments with reference to the attached drawings.

DESCRIPTION OF THE EMBODIMENTS

Figure 1:
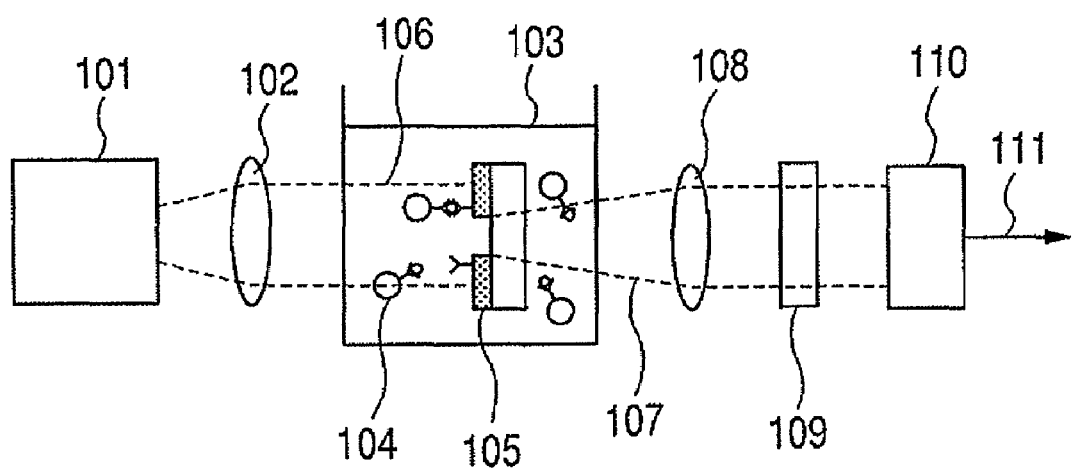
FIG. 1 is a view schematically illustrating the construction of a first exemplary embodiment of the chemical sensing apparatus of the present invention.

In the following are described advantageous exemplary embodiments of the present invention.

The chemical sensing apparatus of the present invention preferably has a construction as follows.

The chemical sensing apparatus of the present invention executes detection by immobilizing a target substance through a bonding with a capturing substance.

The chemical sensing apparatus includes following constituent components: a light source; a metal thin film having an aperture smaller than the wavelength of a light irradiated from the light source, or a metal fine particle smaller than the wavelength of the light; a transparent substrate bearing the metal thin film having the aperture or the metal fine particle on a surface thereof; the capturing substance bonded to a metal surface of the metal thin film in the vicinity of the aperture or to a surface of the metal fine particle; a marker substance combined with the target substance capable of bonding to the capturing substance, and having a dimension of from 1/10 times to 10 times of the dimension of the aperture or the metal fine particle; and a photodetector for detecting, when the light emitted from the light source irradiates the metal thin film having the aperture or the metal fine particle, a transmitted light through the aperture formed in the metal thin film or a scattered light emitted from the metal fine particle.

The chemical sensing apparatus utilizes a following detection method.

The target substance combined with the marker substance is immobilized, by the bonding to the capturing substance, on the metal surface of the metal thin film in the vicinity of the aperture or on the surface of the metal fine particle. When such immobilization is made, the target substance is detected, based on a change generated in the transmitted light through the aperture formed in the metal thin film, or a change generated in the scattered light from the metal fine particle.

The chemical sensing apparatus may adopt a construction in which the marker substance is a dielectric fine particle.

The chemical sensing apparatus may adopt a construction in which the marker substance is a second metal fine particle.

The chemical sensing apparatus may adopt a construction in which the marker substance is a magnetic fine particle.

On the other hand, the photodetector preferably has a construction capable of detecting a spectral shape of the transmitted light through the aperture formed in the metal thin film, or the scattered light emitted from the metal fine particle.

There may be also adopted a construction in which plural such apertures formed in the metal thin film or plural metal fine particles are provided, and such plural apertures or such plural metal fine particles are arranged in a one-dimensional or two-dimensional away on the surface of the transparent substrate.

In such case, the photodetector to be employed is capable of detecting the transmitted light through the plural apertures or the scattered light emitted from the plural metal fine particles, arranged in the one-dimensional or two-dimensional array on the surface of the transparent substrate. For example, employed preferably is a photodetector capable of detection as one-dimensional or two-dimensional image information.

In the above-described chemical sensing apparatus, the irradiating method of the light from the light source and the arrangement of the photodetector preferably have following construction. Such construction is a dark field illumination, in which, when the light from the light source irradiates the metal thin film having the aperture or the metal fine particle, the transmitted light through the aperture formed in the metal thin film or the scattered light from the metal fine particle alone is detected by the photodetector.

Also the chemical sensing apparatus of the present invention may be of a system construction incorporated in a chemical microanalytical system, as a detection unit in a detection portion of the chemical microanalytical system.

Further, the chemical sensing apparatus of the present invention may be of a system construction incorporated in a target substance detecting system utilizing a DNA chip, as a detection unit in a detection portion of the target substance detecting system utilizing a DNA chip.

Further, the chemical sensing apparatus of the present invention may be of a system construction incorporated in a target substance detecting system utilizing a protein chip, as a detection unit in a detection portion of the target substance detecting system utilizing a protein chip.

The chemical sensing method of the present invention preferably has a following construction.

The chemical sensing method of the present invention executes detection by immobilizing a target substance through a bonding with a capturing substance.

The chemical sensing is executed by an apparatus including following constituent components: a light source; a metal thin film having an aperture smaller than the wavelength of a light irradiated from the light source, or a metal fine particle smaller than the wavelength of the light; a transparent substrate bearing the metal thin film having the aperture or the metal fine particle on a surface thereof; the capturing substance bonded to a metal surface of the metal thin film in the vicinity of the aperture or to a surface of the metal fine particle; a marker substance combined with the target substance capable of bonding to the capturing substance and having a dimension of from $1/10$ times to 10 times of the dimension of the aperture or the metal fine particle; and a photodetector for detecting, when the light emitted from the light source irradiates the metal thin film having the aperture or the metal fine particle, a transmitted light through the aperture formed in the metal thin film or a scattered light emitted from the metal fine particle.

The chemical sensing method utilizes a following detection method.

The target substance combined with the marker substance is immobilized, by the bonding to the capturing substance, on the metal surface of the metal thin film in the vicinity of the aperture or on the surface of the metal fine particle. When such immobilization is made, the target substance is detected, based on a change generated in the transmitted light through the aperture formed in the metal thin film, or a change generated in the scattered light from the metal fine particle.

The sensing operations of the chemical sensing method include: immobilizing the target substance, combined with the marker substance, on the metal surface of the metal thin film in the vicinity of the aperture or on the surface of the metal fine particle, through a bonding to the capturing substance; when the immobilization is made, irradiating the metal thin film having the aperture or the metal fine particle with the light from the light source; and in a state of irradiation with the light from the light source, detecting a transmitted light through the aperture formed in the metal thin film or a scattered light from the metal fine particle, by the photodetector.

The chemical sensing method may assume forms listed in the following.

The photodetector may be provided with a function of detecting the spectral shape of the transmitted light through the aperture formed in the metal thin film or the scattered light from the metal fine particle.

Then, in the step of detecting the transmitted light through the aperture formed in the metal thin film or the scattered light from the metal fine particle, by the photodetector, executed is a following operation of detecting the spectral shape of the transmitted light through the aperture formed in the metal thin film or the scattered light from the metal fine particle.

Also the photodetector may be provided with a function of detecting the light from a measurement area having a one-dimensional or two-dimensional spreading, as one-dimensional or two-dimensional image information.

Then, in the step of detecting the transmitted light through the aperture formed in the metal thin film or the scattered light from the metal fine particle by the photodetector, executed is a following operation of detecting the light from an area irradiated with the light from the light source, as one-dimensional or two-dimensional image information.

Also in the chemical sensing method, in the step of detecting the transmitted light through the aperture formed in the metal thin film or the scattered light from the metal fine particle by the photodetector, there may be added an operation of calculating a gradation of a light intensity, based on the result of measurement of the light intensity detected by the photodetector.

Furthermore, in the chemical sensing method, a following substance may be utilized as the capturing substance bonded with the metal surface of the metal thin film in the vicinity of the aperture or with the surface of the metal fine particle. A second light is used to irradiate the metal surface of the metal thin film in the vicinity of the aperture or the surface of the metal fine particle thereby bonding the capturing substance to the metal surface by a photochemical reaction induced by the second light.

In the following, the technical background of the present invention will be described in more details.

On a surface of a flat metal thin film, because of the special character of the surface, there is generated a mode of an electron wave (plasmon) capable of coupling with a light, namely a surface plasmon.

On the other hand, a metal fine particle having a particle size (diameter) smaller than the wavelength of light has an extremely small radius of curvature of the surface, and, when a light enters the surface, the generated diffraction light has a diffraction angle larger than the incident angle. Therefore, there is generated a situation where a diffracted light is not generated, and the light is enclosed within the metal surface. As a result, a near-field light generated on the surface of the metal fine particle causes a coupling with a free electron, thereby generating a localized surface plasmon. An absorption (scattering) derived from a surface plasmon resonance and generated on the surface of such metal fine particle is called a localized surface plasmon resonance.

(First Form)

Figure 2A:
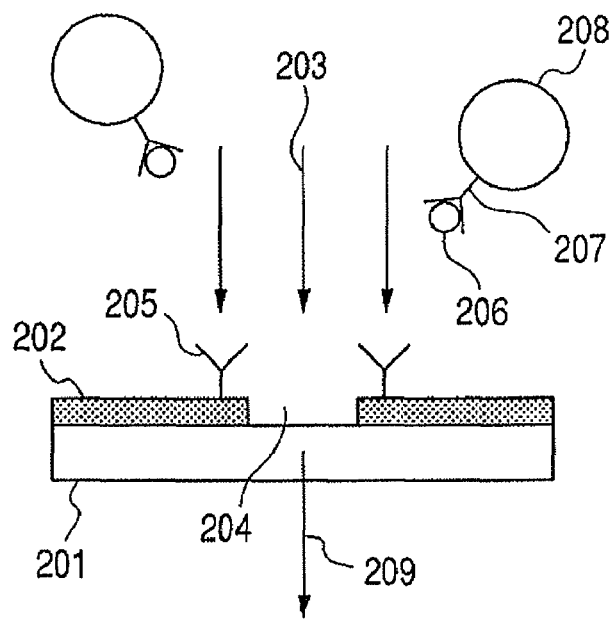
FIGS. 2A and 2B are views schematically illustrating the working principle of a sensing method utilizing a local plasmon resonance generated in a small aperture, in the first exemplary embodiment of the chemical sensing apparatus of the present invention.

In the following, a principle utilized in accomplishing a high detection sensitivity in the chemical sensing apparatus of the present invention will be described. At first, the principle of the detection method, utilized in the first form of the present invention, will be described with reference to FIGS. 2A and 2B. As illustrated in FIG. 2A, in a sensor medium, a small aperture 204 smaller than a wavelength λ of an irradiating light 203 in a metal thin film 202 formed on a transparent substrate 201. In the vicinity of the aperture 204, a molecule 1 (205) of a capturing substance is bonded. On the other hand, on a target substance 206, a marker substance 208 of a size comparable to that of the aperture 204 is bonded across a molecule 2 (207) of the capturing substance.

More specifically, the size of the marker substance 208 is selected, with respect to the size of the aperture 204, within a range of from 1/10 times to 10 times and preferably from 1/3 times to 3 times.

The magnitude of a near-field light interaction, generated between two objects irradiated with a light, becomes largest when the two objects have comparable sizes, but becomes smaller when either one of the two objects is larger or smaller.

In the present invention, therefore, the size of the aperture and the size of the marker substance are made comparable (from 1/10 times to 10 times and preferably from 1/3 times to 3 times). In this manner, the near-field light interaction, generated between the aperture and the marker substance, can be increased. Thus, the change in the near-field distribution in the vicinity of the aperture can be increased when the marker substance approaches the aperture.

Figure 2B:
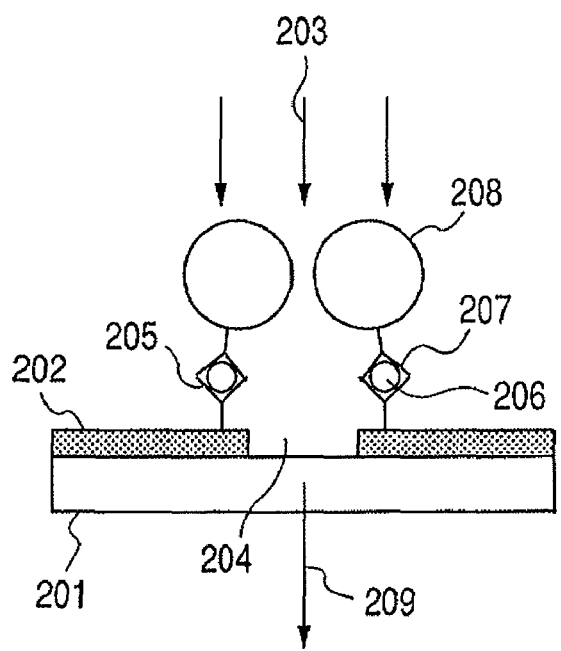

The sensor medium is immersed in a specimen solution containing the target substance molecule 206, combined with the marker substance 208, thereby executing a reaction between the capturing substance molecule 1 (205) and the target substance molecule 206. As illustrated in FIG. 2B, the target substance molecule 206, combined with the marker substance 208, is immobilized, by the capturing substance molecule 2 (207), in the vicinity of the aperture 204. Thus, there is obtained a construction where the marker substance 208 is positioned close to the aperture 204.

The metal thin film 202, including the aperture 204, has a thickness of from 10 nm to 1 μm. The size of the aperture 204 may be selected smaller than the wavelength λ of the irradiating light 203. However, it is preferably selected in the following manner.

As to the planar shape of the aperture 204, among the longitudinal and transversal dimensions, the shorter one is selected equal to or less than the wavelength λ, preferably equal to or less than 1/2 of the wavelength λ. On the other hand, the size of the aperture 204, formed equal to or less than 1/100 of the wavelength λ, may cause a problem in the precision. For example in the case of λ=500 nm and in the case that the aperture 204 is formed with 1/100 of the wavelength λ or less, the size of the aperture 204 becomes 5 nm. It is therefore generally desirable to select the size within a range that does not become equal to or less than 1/50 of the wavelength λ.

When the irradiating light 203 is introduced vertically to the upper surface of the metal thin film 202 provided with the aperture 204, a transmitted light 209 has a transmission spectrum resulting from a localized surface plasmon resonance corresponding to the shape of the aperture 204 (longitudinal and transversal widths of the aperture, thickness of the metal thin film and metal material). In a state where the capturing substance molecule 1 (205) is bonded to the vicinity of the aperture 204, a peak resulting from the localized surface plasmon resonance has a peak wavelength $\lambda_1$.

Figure 4:
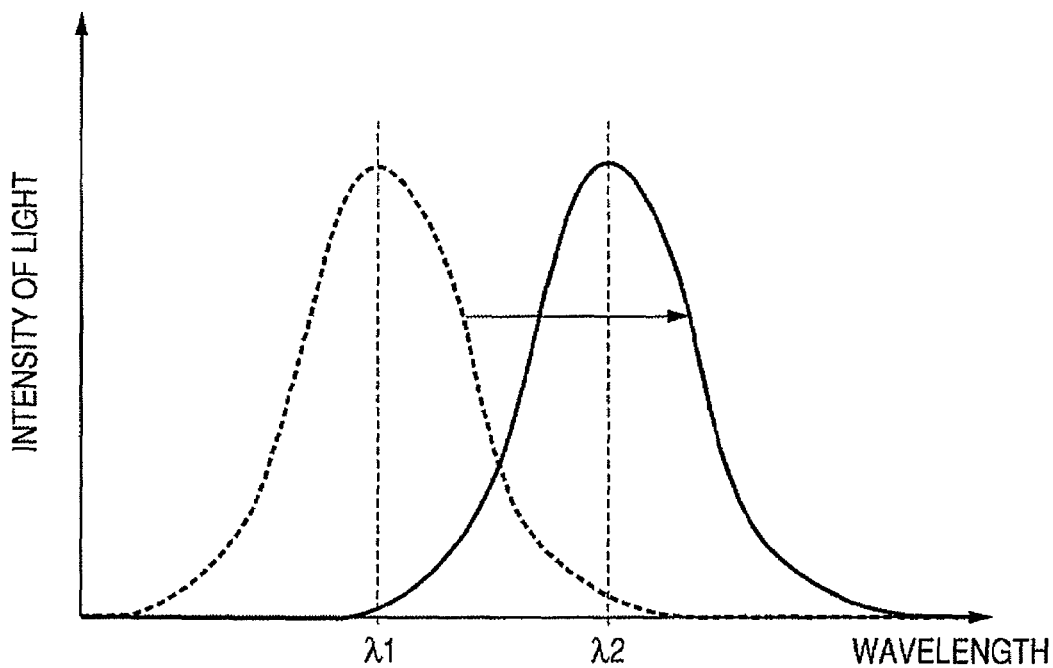
FIG. 4 is a view schematically illustrating a shift in a peak wavelength, in a spectrum of a light absorption (or light scattering) resulting from a plasmon resonance on a metal surface, by a substance adsorption on the metal surface.

On the other hand, in a state where the target substance 206, combined with the marker substance 208, is immobilized by the capturing substance molecule 2 (207), the peak resulting from the localized surface plasmon resonance has a peak wavelength $\lambda_2$. FIG. 4 schematically illustrates a mode of shifting of the peak wavelength of the peak resulting from the localized surface plasmon resonance, caused by immobilization of the target substance 206 combined with the marker substance 208.

Such localized surface plasmon resonance is a phenomenon characteristic of the vicinity of the aperture 204. Therefore, the aforementioned shift in the peak wavelength is induced by the bonding, to the capturing substance molecule 1 (205) in the vicinity of the aperture 204, of a single molecule of the target substance molecule 206 combined with the marker substance 208. Reflecting the shift in the peak wavelength of the peak resulting from the localized surface plasmon resonance, a change also occurs in the spectral shape of the transmitted light through the aperture 204. Therefore, the detection of the change in the spectral shape of the transmitted light through the aperture 204 allows to detect presence/absence of the bonding of the target substance molecule 206, combined with the marker substance 208, to the capturing substance molecule 1 (205) in the vicinity of the aperture 204, in the level of a single molecule.

The peak wavelength shift in the peak resulting from the localized surface plasmon resonance has only a small shift amount in a state where the target substance molecule 206 alone is bonded to the capturing substance molecule 1 (205), since the target substance molecule 206 is of a small size. On the other hand, when the target substance molecule 206 combined with the marker substance 208 is bonded with the capturing substance molecule 1 (205), the shift amount becomes larger as the size of the marker substance 208 is significantly larger than that of the target substance molecule 206.

The present invention, utilizing the increase in the shift amount of the peak wavelength in the peak resulting from the localized surface plasmon resonance, enables to detect the change in the spectral shape of the transmitted light 209 through the aperture 204, with a higher sensitivity.

(Second Form)

Figure 3A:
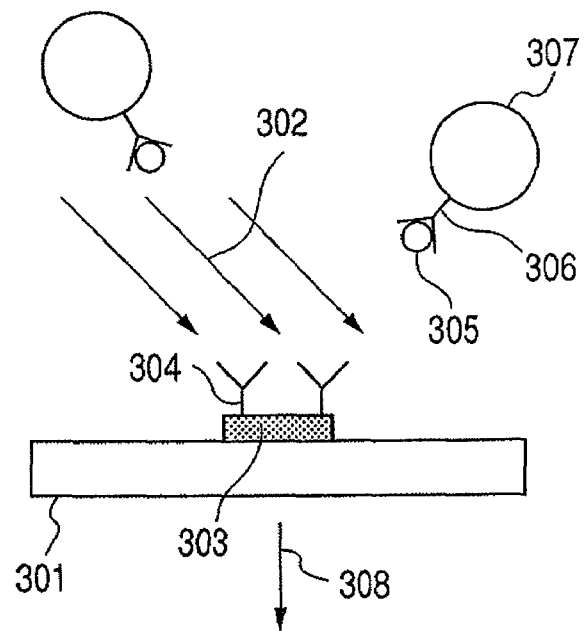
FIGS. 3A and 3B are views schematically illustrating the working principle of a sensing method utilizing a local plasmon resonance generated on a surface of a metal fine particle, in a second exemplary embodiment of the chemical sensing apparatus of the present invention.

In the following, the principle of the detection method, utilized in the second form of the present invention, will be described with reference to FIGS. 3A and 3B. The second form of the present invention utilizes a metal fine particle, in place for the small aperture formed in the metal thin film. As illustrated in FIG. 3A, a metal fine particle 303 of a size smaller than the wavelength λ of the irradiating light 303 is formed on a transparent substrate 301. On the surface of the metal fine particle 303, a capturing substance molecule 1 (304) is bonded. On the other hand, a marker substance 307 of a size comparable to that of the metal fine particle 303 is bonded to the target substance 305, by means of a capturing substance molecule 2 (306).

More specifically, the size of the marker substance 307 is selected, with respect to the size of the metal fine particle 303, within a range of from 1/10 times to 10 times and preferably from 1/3 times to 3 times.

The magnitude of a near-field light interaction, generated between two objects irradiated with a light, becomes largest when the two objects have comparable sizes, but becomes smaller when either one of the two objects is larger or smaller.

In the present invention, therefore, the size of the metal fine particle and the size of the marker substance are made comparable (from 1/10 times to 10 times and preferably from 1/3 times to 3 times). In this manner, the near-field light interaction, generated between the metal fine particle and the marker substance, can be increased. Thus, the change in the near-field distribution in the vicinity of the metal fine particle can be increased when the marker substance approaches the metal fine particle.

The sensor medium is immersed in a specimen solution containing the target substance molecule 305, combined with the marker substance 307, thereby executing a reaction between the capturing substance molecule 1 (304) and the target substance molecule 305 combined with the marker substance 307. As illustrated in FIG. 3B, the target substance molecule 305, combined with the marker substance 307, is immobilized, by the capturing substance molecule 2 (306), on the surface of the metal fine particle 303. Thus, there is obtained a construction where the marker substance 307 is positioned close to the metal fine particle 303.

The metal thin film constituting the metal fine particle 303 has a thickness of from 10 nm to 1 μm. The size of the metal fine particle 303 may be selected smaller than the wavelength $\lambda$ of the irradiating light 302. However, it is preferably selected in the following manner.

As to the planar shape of the metal fine particle 303, among the longitudinal and transversal dimensions, the shorter one is selected equal to or less than the wavelength $\lambda$, preferably equal to or less than 1/2 of the wavelength $\lambda$. On the other hand, the size of the metal fine particle 303, formed equal to or less than 1/100 of the wavelength $\lambda$, may cause a problem in the precision. For example in the case of the wavelength $\lambda$=500 nm and in the case that the metal fine particle 303 is formed with 1/100 of the wavelength $\lambda$ or less, the size of the metal fine particle 303 becomes 5 nm. It is therefore generally desirable to select the size within a range that does not become equal to or less than 1/50 of the wavelength $\lambda$.

The irradiating light 302 is introduced obliquely to the upper surface of the metal fine particle 303, in order to avoid the influence of a directly transmitted light. Under the irradiation by the irradiating light 302, a scattered light 308 from the metal fine particle 303 has an absorption spectrum resulting from a localized surface plasmon resonance corresponding to the shape of the metal fine particle 303 (longitudinal and transversal widths and thickness of the metal fine particle, and metal material). In a state where the capturing substance molecule 1 (304) is bonded on the surface of the metal fine particle 303, a peak resulting from the localized surface plasmon resonance has a peak wavelength $\lambda_1$.

On the other hand, in a state where the target substance molecule 305, combined with the marker substance 307, is immobilized by the capturing substance molecule 2 (306), the peak resulting from the localized surface plasmon resonance has a peak wavelength $\lambda_2$.

Such localized surface plasmon resonance is a phenomenon characteristic of the vicinity of the surface of the metal fine particle 303. Therefore, the aforementioned shift in the peak wavelength is induced by the bonding, to the capturing substance molecule 1 (304) on the surface of the metal fine particle 303, of a single molecule of the target substance molecule 305 combined with the marker substance 307. Reflecting the shift in the peak wavelength of the peak resulting from the localized surface plasmon resonance, a change also occurs in the spectral shape of the scattered light 308 from the rear surface of the metal fine particle 303. Therefore, the detection of the change in the spectral shape of the scattered light 308 from the metal fine particle 303 allows to detect presence/absence of the bonding of the target substance molecule 305, combined with the marker substance 307, to the capturing substance molecule 1 (304) on the surface, in the level of a single molecule.

The peak wavelength shift in the peak resulting from the localized surface plasmon resonance has only a small shift amount in a state where the target substance molecule 305 alone is bonded to the capturing substance molecule 1 (304), since the target substance 305 is of a small size. On the other hand, when the target substance molecule 305 combined with the marker substance 307 is bonded with the capturing substance molecule 1 (304), the shift amount becomes larger as the size of the marker substance 307 is significantly larger than that of the target substance molecule 305.

The present invention, utilizing the increase in the shift amount of the peak wavelength in the peak resulting from the localized surface plasmon resonance, enables to detect the change in the spectral shape of the scattered light 308 emitted from the rear surface of the metal fine particle 303 with a higher sensitivity.

The irradiating light 302 is obliquely introduced into the upper surface of the metal fine particle 303, and the scattered light 308 from the rear side is observed from the perpendicular direction. Such arrangement of dark field illumination enables to prevent, in the detection of the scattered light 308, the influence of the directly transmitted light of the irradiating light 302. For example, when the irradiating light 302 is obliquely introduced onto the upper surface of the metal fine particle 303, the incident angle may be selected within a range of satisfying a totally reflecting condition.

The present invention utilizes a localized surface plasmon resonance, caused by a coupling of a near-field light, that is induced by the irradiating light 302 obliquely entering the surface of the metal fine particle 303 and is generated on the surface of the metal, and a free electron of the metal. If the marker substance 307 is immobilized at a distance, from the surface of the metal fine particle, shorter than the magnitude of the metal fine particle, the electron wave generated on the metal surface is influenced. Therefore, a significant change is induced in the resonance condition (resonance frequency) of the localized surface plasmon resonance.

As the marker substance 208 or 307, selected is a fine dielectric substance such as a polystyrene bead, a fine metal substance such as a gold nanoparticle, or a fine magnetic substance such as a nanoferrite bead.

In case of employing the fine metal substance, a strong modulation can be applied to the local surface plasmon excited in the vicinity of the aperture 204 under the irradiation with the irradiating light 203, or to the local surface plasmon excited in the vicinity of the metal fine particle 303 under the irradiation with the irradiating light 302. This is because an electric field, generated between the fine metal substance and the metal fine particle, is intensified thereby exhibiting a new mode of the local surface plasmon in an integral structure of the fine metal substance and the metal fine particle. Such modulating effect can be utilized to achieve an effect of enabling the sensing of a higher sensitivity.

In case of employing the fine magnetic substance, a magnet can be used to collect and concentrate the target substance, bonded with the fine magnetic substance. Also in the reaction with the capturing substance molecule 1, the target substance 208 combined with the fine magnetic substance can be attracted to the vicinity of the aperture 204. Such feature can be utilized to achieve an effect that even the target substance molecule 206, combined with the fine magnetic substance and contained in a low concentration in the specimen liquid, can be efficiently bonded to the capturing substance molecule and can be detected.

Also by changing the size of the marker substance 208, 307 according to the type of the target substance 206, 305, plural target substances can be detected simultaneously as the amount of spectral change is different for each substance.

In order to bond the capturing substance molecule 1 (205) specifically in the vicinity of the aperture 204, the rear surface of the transparent substrate 201 is irradiated with another light, and near-field light oozing out on the top surface side of the aperture 204 is used to induce a photochemical reaction thereby selectively bonding the capturing substance molecule 1 (205). It is thus possible to bond the capturing substance molecule 1 (205) specifically in the vicinity of the aperture 204 and not to cause bonding in other portions. As a result, a chemical sensing of a higher sensitivity is made possible.

Examples of the photochemical reaction includes a photocrosslinking reaction, a radical photopolymerization reaction and a cationic photopolymerization reaction by a photoradical generation, a photoacid generation or a photoamine generation as employed in a photoresist system. Thus the capturing substance molecule 1 can be chemically bonded to the metal constituting the aperture 204, either directly or across a surface oxide film, a silane coupling agent molecule, an alkanethiol film and the like.

Similarly, in order to bond the capturing substance molecule 1 (304) specifically on the metal fine particle 303, the metal fine particle 303 is irradiated with another light, and near-field light oozing out on the top surface metal fine particle is used to induce a photochemical reaction thereby bonding the capturing substance molecule 1 (304). This method enables to bond the capturing substance molecule 1 (304) specifically on the metal fine particle, particularly in a portion having a high intensity of the near-field light and not to cause bonding in other portions. As a result, a chemical sensing of a higher sensitivity is made possible.

In the following, the present invention will be clarified further by specific examples. The modes described in the following are examples of embodiments, but the technical scope of the present invention is not limited to such exemplary embodiments.

First Exemplary Embodiment

In the following, a first exemplary embodiment of the chemical sensing apparatus of the present invention will be described with reference to FIG. 1.

In the construction illustrated in FIG. 1, a tungsten lamp, a light-emitting diode or the like is utilized as a light source 101.

An irradiating light 106 (having a wavelength λ within a range of from 500 to 1,300 nm) emitted from the light source 101 irradiates a sensor medium 105 through a collimating lens 102. The sensor medium 105 has a construction having a metal thin film of a thickness of 50 nm, formed on a surface of a substrate that is translucent to the irradiating light 106. The metal thin film includes an aperture of a rectangular shape, having a longitudinal dimension of 200 nm and a transversal dimension of 50 nm as illustrated in FIGS. 2A and 2B. The smaller one of the longitudinal and transversal sizes of the aperture is made smaller than the wavelength λ of the irradiating light 106 and is equal to or smaller than ½ of the wavelength λ.

A capturing substance, having a bonding ability to a target substance, is immobilized in the vicinity of the small aperture. As such capturing substance having a bonding ability to a target substance, an antibody molecule can be utilized advantageously. The antibody molecule can be selectively bonded to an antigen molecule constituting the target substance, through an antigen-antibody reaction.

On the other hand, a specimen liquid 103 contains a target substance 104 combined with a marker substance. The target substance 104 combined with the marker substance is in a state, for example, that a marker substance such as a polystyrene bead of a diameter of 50 nm is combined to the target substance such as an antigen molecule. In the target substance 104 combined with a marker substance, the ratio of marker substance and target substance is selected as 1:1.

The size of the polystyrene bead usable as the marker substance has to be selected within a range of from 5 to 500 nm, preferably from 15 to 150 nm, namely, in comparison with 50 nm which is the smaller transversal size of the aperture, within a range of from 1/10 to 10 times, preferably from 1/3 to 3 times. In the present example, it is selected as 50 nm.

Also a solvent constituting the specimen liquid 103 is an aqueous solvent, such as a buffer solution, of which the refractive index $n_{solvent}(\lambda)$ at the wavelength λ of the irradiating light 106 can be regarded as equal to the refractive index of water $n_{H2O}(\lambda)$ which is 1.33-1.34. On the other hand, polystyrene employed in the polystyrene bead has a refractive index $n_{polystyrene}(\lambda)$ within a range of from 1.54-1.56. Thus polystyrene and the buffer solution (water) has a difference in the refractive index, and the polystyrene bead of a small diameter, when approaching the small aperture in the buffer solution, causes a change in the refractive index of the vicinity.

In the material of the metal thin film to be used in the preparation of the sensor medium 105, in a buffer solution (refractive index $n_{H2O}(\lambda)$=1.33-1.34), the peak wavelength of the localized surface plasmon resonance of such metal, namely, $\lambda_{localized\ surface\ plasmon}(\lambda)$ ($n_{H2O}(\lambda)$=1.33), is desirably present within a range of from 400 to 1,300 nm.

Among the metal materials satisfying this condition, a material capable of withstanding the use in the buffer solution is selected. For example, when immersed in the buffer solution, if a chemical reaction takes place on the metal thin film itself and causes a dissolution of the metal, there may result a decrease in the film thickness thereof or an increase in the size of the aperture. Otherwise, when immersed in the buffer solution, if a chemical reaction takes place on the metal thin film itself and causes formation of a surface oxide film, there may result a state where a metal oxide film is laminated on the surface of the metal thin film.

For example gold (Au) has refractive indexes $n_{Au}(\lambda)$ of $n_{Au}(\lambda=500\ nm)=0.803$ and $n_{Au}(\lambda=700\ nm)=0.131$. Silver (Ag) has refractive indexes $n_{Au}(\lambda)$ of $n_{Ag}(\lambda=376\ nm)=0.090$ and $n_{Ag}(\lambda=500\ nm)=0.0468$. Copper (Cu) has refractive indexes $n_{Cu}(\lambda)$ of $n_{Cu}(\lambda=500\ nm)=1.03$ and $n_{Cu}(\lambda=750\ nm)=0.103$. Aluminum (Al) has refractive indexes $n_{Al}(\lambda)$ of $n_{Al}(\lambda=220\ nm)=0.14$ and $n_{Al}(\lambda=400\ nm)=0.40$. Also the peak wavelength of the surface plasmon resonance $\lambda_{surface\ plasmon}$ ($n_0=1.00$) is 526 nm in gold (Au), 320 nm in silver (Ag), 550 nm in copper (Cu), and 120 nm in aluminum (Al). Also in a buffer solution designed to set the pH within a range of from 6.5 to 8.0, the chemical reaction to these metals is quite limited. Therefore, gold, silver, copper or aluminum can be advantageously used as the material of the metal thin film for constructing the sensor medium 105.

In addition, on a metal thin film of gold, silver, copper or aluminum, the localized surface plasmon resonance induced by the surface plasmon generated thereon has a high intensity and adapted for the purpose of the present invention. When a substance is adsorbed on the metal thin film, the peak wavelength of the localized surface plasmon resonance $\lambda_{localized\ surface\ plasmon}$ is generally observed at a longer wavelength side of the peak wavelength of the surface plasmon resonance $\lambda_{surface\ plasmon}$ ($n_0=1.00$). In particular, in case of utilizing a gold thin film and when a substance adsorption takes place on the gold thin film, the peak wavelength of the localized surface plasmon resonance $\lambda_{localized\ surface\ plasmon}$ is present in a visible region longer than 526 nm, so that it is suitable for a construction of selecting the wavelength $\lambda$ of the irradiating light 106 in the visible region.

On the other hand, an alloy among gold, silver, copper and aluminum may be utilized as the metal thin film. As the alloy among gold, silver, copper and aluminum is capable of forming a uniform solid solution, the composition thereof may be selected arbitrarily. In case of utilizing an alloyed metal thin film, the peak wavelength of the surface plasmon resonance $\lambda_{surface\ plasmon}$ is generally present within a wavelength range having the peak wavelengths, observed respectively for the component metals of the alloy, at both ends. This property can be utilized, for example in case of an alloy of gold (Au) and silver (Ag), to regulate the peak wavelength of the surface plasmon resonance $\lambda_{surface\ plasmon}$ within a range of from 320 to 526 nm. Thus, a metal thin film formed by an alloy among gold, silver, copper and aluminum enables, in addition to a regulation of the aperture shape such as longitudinal dimension, transversal dimension, thickness and gap, to regulate the peak wavelength of the localized surface plasmon $\lambda_{localized\ surface\ plasmon}$ within a range from a near ultraviolet region to a near infrared region. Therefore, this method enables to regulate the peak wavelength of the localized surface plasmon $\lambda_{localized\ surface\ plasmon}$ over the entire range from 350 to 1,600 nm.

In the rectangular aperture of a longitudinal dimension of 200 nm and a transversal dimension of 50 nm formed in the metal thin film, a density $D_1$ of the capturing substance bonded to the vicinity thereof is preferably selected at least at $D_1=10,000$ molecule/$\mu m^2$ or higher. More specifically, a small area of the metal surface of a longitudinal dimension of 300 nm and a transversal dimension of 150 nm, having the rectangular aperture of a longitudinal dimension of 200 nm and a transversal dimension of 50 nm at the center thereof, has an area of 0.045 $\mu m^2$. It is preferable that, within such small area, the capturing substance is bonded by at least $N_1=D_1\times 0.045=450$ molecules. Stated differently, it corresponds to an average distance $d_1$ of the adjacent capturing substances of $1000/(D_1)^{1/2}$ $\mu m \cong 10$ nm or less.

An area where the capturing substance is bonded is desirably an area in the vicinity of the rectangular aperture of longitudinal dimension of 200 nm and transversal dimension of 50 nm and within a distance from an end portion of the rectangular aperture to about the size of the marker substance, or less. This is because the marker substance positioned close to the aperture provides an evident influence on the near-field light distribution in the vicinity of the aperture. Therefore, in case of utilizing polystyrene beads of 50 nm as the marker substance in combination with the rectangular aperture of a longitudinal dimension of 200 nm and a transversal dimension of 50 nm, the bonding of the capturing substance is desirably conducted in an area of 300 nm×150 nm or less. The bonding of the capturing substance on this small area can be executed, as described above, by a method of irradiating the rear surface of the substrate having the aperture with another light, and inducing a photochemical reaction by the near-field light oozing out on the top surface side of the aperture thereby selectively bonding the capturing substance molecule.

On the other hand, the target substance 104 combined with the marker substance is prepared in a state in which the marker substance such as a polystyrene bead of a diameter of 50 nm is combined to the target substance such as an antigen molecule with a ratio of marker substance:target substance of 1:1 as described above. Now an example of the method of quantitatively bonding the marker substance with the target substance will be described. As illustrated in FIGS. 2A and 2B, a composite molecule in which a second capturing substance (capturing substance 2) and a marker substance are combined quantitatively is prepared separately. The composite molecule is reacted with the target substance in a liquid phase to bond the target substance to the portion of the second capturing substance (capturing substance 2) thereby obtaining a combined state with a ratio of marker substance target substance of 1:1.

The reaction in the liquid phase corresponds to a composite forming reaction between the composite molecule in which the second capturing substance (capturing substance 2) and the marker substance are combined quantitatively, and the target substance molecule. Therefore, a concentration $C_2$ of the composite molecule in which the second capturing substance 2 and the marker substance are combined, a concentration $C_0$ of the free target substance molecule, and a concentration $C_1$ of the target substance 104 combined with the marker substance follow a dissociation equilibrium of the composite. These can be represented as $K_1=(C_0\times C_2)/C_1$, wherein $K_1$ is a dissociation equilibrium constant of the composite. A ratio $C_1/C_0$ of the concentration $C_1$ of the target substance 104 combined with the marker substance and the concentration $C_0$ of the free target substance molecule is represented by $\{C_1/C_0\}=C_2/K_1$.

In the present invention, in the specimen solution 103, the ratio $C_1/C_0$ of the concentration $C_1$ of the target substance 104 combined with the marker substance and the concentration $C_0$ of the free target substance molecule preferably satisfies at least a condition $C_1/C_0 \geqq 10$. In order to maintain this condition, it is necessary to add, in the specimen solution 103, the composite molecule in which the capturing substance 2 and the marker substance are combined at a concentration satisfying a condition $C_2/K_1 \geqq 10$.

Otherwise, after the second capturing substance (capturing substance 2) and the target substance molecule are combined, a process is executed to bond them both by a covalent bonding, thereby hindering the progress of dissociation. In case of executing such covalent bonding process, the composite molecule in which the capturing substance 2 and the marker substance are combined need not be present in the specimen solution 103.

When the sensor medium 105 is immersed in the specimen solution 103, as illustrated in FIGS. 2A and 2B, the target substance (206) in the target substance 104 combined with the marker substance is bonded by the capturing substance (205) bonded in the vicinity of the rectangular aperture formed in the metal thin film. The irradiating light from the light source 101 is formed into a parallel beam by the collimating lens 102 and is introduced to the sensor. The irradiating light 106 is vertically introduced from the upper surface of the metal thin film of the sensor medium 105, in a state where the target substance 104 combined with the marker substance is bonded by the capturing substance. On the other hand, a detection system for the transmitted light is constituted of a condenser lens 108, an interference filter 109, and a photodetector 110. The condenser lens 108 is so positioned that the focal point thereof can condense the light transmitted by the rectangular aperture, formed in the metal thin film of the sensor medium 105. More specifically, a light transmitted by the rectangular aperture, at the interface between the metal thin film and the transparent substance of the sensor medium 105, is formed into a parallel light beam by the condenser lens 108 and enters the interference filter 109.

The interference filter 109 is a so-called Fabry-Perot type interference filter and is capable of transmitting the light of a specified wavelength only. A spectrometer function is provided by utilizing a characteristic that the transmittable wavelength can be changed by changing the incident angle of the incident light to the surface of the Fabry-Perot type interference filter. An intensity of the light of a specified wavelength, separated by the interference filter 109, is detected by the photodetector 110. The result of measurement of the optical intensity of the thus separated specified wavelength is output as a detection signal 111. In practice, the detection signal 111 contains information of the specified wavelength $\lambda$ separated by the interference filter 109 and a detected optical intensity $P(\lambda)$ at such wavelength. A spectrum of the transmitted light can be obtained by plotting the wavelength $\lambda$ of the information $(\lambda, P(\lambda))$ on the abscissa and the detected optical intensity $P(\lambda)$ on the ordinate.

Since the irradiating light 106 in a parallel beam state is vertically introduced to the metal thin film of the sensor medium 105, the light entering the metal thin film, other than the vicinity of the small rectangular aperture, is reflected by the metal surface. Therefore, in the detection system of the aforementioned construction, detected in principle is a transmitted light 107 only, transmitted by the small rectangular aperture.

The transmitted light 107, transmitted by the small rectangular aperture, contains a component dependent on the localized surface plasmon resonance in the small aperture formed in the metal thin film. The component of the transmitted light dependent on the localized surface plasmon resonance exhibits a wavelength distribution (spectrum) dependent on a local change in the refractive index by the molecule immobilized in the vicinity of the small rectangular aperture. More specifically, the transmitted light component dependent on the localized surface plasmon resonance has different peak wavelengths in a state where the capturing substance is bonded to the vicinity of the small rectangular aperture and in a state where the target substance is bonded to the capturing substance. Also the transmitted light component dependent on the localized surface plasmon resonance has different peak wavelengths in a state where the target substance is bonded to the capturing substance and in a state where the target substance 104, combined with the marker substance is bonded to the capturing substance. Taking the state where the capturing substance is bonded as a reference, a shift amount of the peak wavelength becomes significantly larger in the state where the target substance 104 combined with the marker substance is bonded to the capturing substance, in comparison with the state where the target substance is bonded to the capturing substance.

In an actual state, in the vicinity of the small rectangular aperture, a portion of a state bonded to the capturing substance and a portion of a state where the capturing substance is bonded with the target substance 104 combined with marker substance are mixedly present. As a result, the transmitted light component dependent on the localized surface plasmon resonance becomes a sum of a component derived from the portion of the state bonded to the capturing substance and a component derived from the portion of the state where the capturing substance is bonded with the target substance 104 combined with the marker substance.

The present invention enables to observe these two components separately, utilizing the larger shift amount of the peak wavelength in the state where the target substance 104 combined with the marker substance is bonded to the capturing substance. As schematically illustrated in FIG. 4, a peak wavelength $\lambda_1$ of the component derived from the portion of the state bonded to the capturing substance and a peak wavelength $\lambda_2$ of the component derived from the portion of the state where the capturing substance is bonded with the target substance 104 combined with the marker substance are separated from each other. In such state, the ratio of the optical intensity $P(\lambda_2)$ of the transmitted light component observed at the wavelength $\lambda_2$ and the optical intensity $P(\lambda_1)$ of the transmitted light component observed at the wavelength $\lambda_1$ reflects a proportion of the portion of the state where the target substance 104, combined with the marker substance, is bonded to the capturing substance.

In the construction illustrated in FIG. 1, the transmitted light 107 alone, transmitted by the small rectangular aperture, can be detected in principle by the use of the interference filter 109. The spectrum of the transmitted light may also be measured in a construction utilizing a spectrometer, instead of the interference filter 109, in such an arrangement of detecting a parallel light beam only.

In the sensor medium 105, the combination of the capturing substance and the target substance may be selected in various manner, so far as the capturing substance can selectively bond and immobilize the target substance. More specifically, applicable are combinations utilized in various sensors, utilizing the selective bonding ability of the capturing substance to the target substance. Examples of such sensor include chemical sensors, including biosensors such as an enzyme sensor, a microorganism sensor, an organella sensor, a tissue sensor, an immunosensor, an enzyme immunosensor, and a bioaffinity sensor. Also it is essential the target substance can be combined with the marker substance and that the target substance combined with the marker substance satisfies a condition that it can be bonded by the capturing substance.

Second Exemplary Embodiment

In the following, a second exemplary embodiment of the chemical sensing apparatus of the present invention will be described with reference to FIG. 5. In the construction illustrated in FIG. 5, a tungsten lamp, a light-emitting diode or the like is utilized as a light source 501. An irradiating light 506 (having a wavelength $\lambda$ within a range of from 500 to 1,300 nm) emitted from the light source 501 irradiates a sensor medium 505 through a collimating lens 502. The sensor medium 505 has a construction having a metal fine particle, formed on a surface of a substrate that is translucent to the irradiating light 506. The metal fine particle has a size of a longitudinal dimension of 200 nm, a transversal dimension of 50 nm and a height of 50 nm, and is adhered on the bottom surface thereof to the surface of the transparent substrate. The smaller one of the longitudinal and transversal sizes in the planar shape of the metal fine particle is made smaller than the wavelength $\lambda$ of the irradiating light 506 and is equal to or smaller than ½ of the wavelength $\lambda$. A capturing substance, having a bonding ability to a target substance, is immobilized on the surface of the metal fine particle. As such capturing substance having a bonding ability to a target substance, an antibody molecule can be utilized advantageously.

On the other hand, a specimen liquid 503 contains a target substance 504 combined with a marker substance. The target substance 504 combined with the marker substance is in a state, for example, that a marker substance such as a polystyrene bead of a diameter of 50 nm is combined to the target substance such as an antigen molecule. In the target substance 504 combined with a marker substance, the ratio of marker substance and target substance is selected as 1:1. The size of the polystyrene bead usable as the marker substance has to be selected within a range of from 5 to 500 nm, preferably from 15 to 150 nm, namely, in comparison with 50 nm which is the smaller transversal size in the planar shape of the metal fine particle, within a range of from $1/10$ to 10 times, preferably from $1/3$ to 3 times. In the present example, it is selected as 50 nm.

Also a solvent constituting the specimen liquid 503 can be similar to that in the aforementioned specimen solution 103.

Also the material of the metal fine particle to be used in the preparation of the sensor medium 505 can be similar to that of the metal thin film used in the preparation of the sensor medium 105.

Also a density $D_2$ of the capturing substance, bonded on the surface of the longitudinal dimension of 200 nm and the transversal dimension of 50 nm of the metal fine particle, is preferably selected at least at $D_2=10,000$ molecule/$\mu m^2$ or higher. More specifically, a cuboid metal surface having the longitudinal dimension of 200 nm, the transversal dimension of 50 nm and the height of 50 nm becomes 0.035 $\mu m^2$. It is preferable that, within such small area, the capturing substance is bonded by at least $N_2=D_2 \times 0.035=350$ molecules. Stated differently, it corresponds to an average distance $d_1$ of the adjacent capturing substances of $1000/(D_2)^{1/2}$ $\mu m \approx 10$ nm or less.

In order to bond the capturing substance onto the surface of the small metal fine particle, utilizable is a method of forming a bond on the metal surface, by chemically reacting a solution, containing the capturing substance, utilizing a silane coupling agent molecule or an alkanethiol film. Also the aforementioned photochemical reaction may be utilized.

On the other hand, the target substance 504 combined with the marker substance is prepared in a state in which the marker substance such as a polystyrene bead of a diameter of 50 nm is combined to the target substance such as an antigen molecule with a ratio of marker substance:target substance of 1:1 as described above. Now an example of the method of quantitatively bonding the marker substance with the target substance will be described. As illustrated in FIGS. 3A and 3B, a composite molecule in which a second capturing substance (capturing substance 2) and a marker substance are combined quantitatively is prepared separately. The composite molecule is reacted with the target substance in a liquid phase to bond the target substance to the portion of the second capturing substance (capturing substance 2) thereby obtaining a combined state with a ratio of marker substance target substance of 1:1.

The reaction in the liquid phase corresponds to a composite forming reaction between the composite molecule in which the second capturing substance (capturing substance 2) and the marker substance are combined quantitatively, and the target substance molecule. Therefore, a concentration $C_2$ of the composite molecule in which the second capturing substance 2 and the marker substance are combined, a concentration $C_0$ of the free target substance molecule, and a concentration $C_1$ of the target substance 504 combined with the marker substance follow a dissociation equilibrium of the composite. These can be represented as $K_1=(C_0 \times C_2)/C_1$, wherein $K_1$ is a dissociation equilibrium constant of the composite. A ratio $C_1/C_0$ of the concentration $C_1$ of the target substance 504 combined with the marker substance and the concentration $C_0$ of the free target substance molecule is represented by $\{C_1/C_0\}=C_2/K_1$.

In the present invention, in the specimen solution 503, the ratio $C_1/C_0$ of the concentration $C_1$ of the target substance 504 combined with the marker substance and the concentration $C_0$ of the free target substance molecule preferably satisfies at least a condition $C_1/C_0 \geq 10$. In order to maintain this condition, it is necessary to add, in the specimen solution 503, the composite molecule in which the capturing substance 2 and the marker substance are bonded at a concentration satisfying a condition $C_2/K_1 \geq 10$.

Otherwise, after the second capturing substance (capturing substance 2) and the target substance molecule are combined, a process is executed to bond the both by a covalent bonding, thereby hindering the progress of dissociation. In case of executing such covalent bonding process, the composite molecule in which the capturing substance 2 and the marker substance are combined need not be present in the specimen solution 503.

Figure 3B:
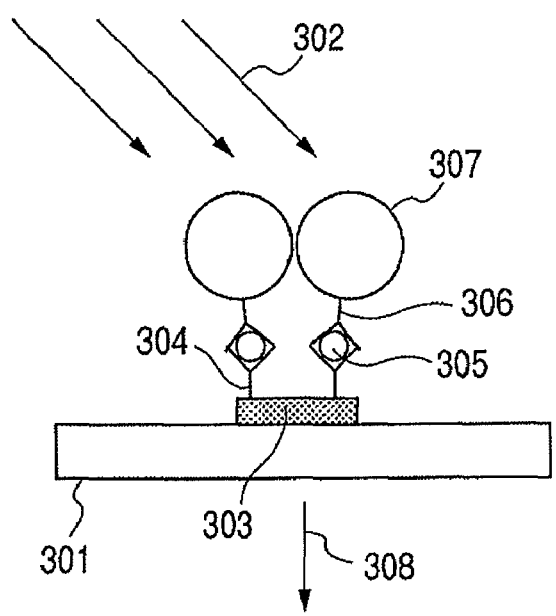

When the sensor medium 505 is immersed in the specimen solution 503, as illustrated in FIGS. 3A and 3B, the target substance (305) in the target substance 504 combined with the marker substance is bonded by the capturing substance (304) bonded to the surface of the metal fine particle. The irradiating light from the light source 501 is formed into a parallel beam by the collimating lens 502 and is introduced to the sensor. The irradiating light 506 is obliquely introduced to the upper surface of the metal fine particle of the sensor medium 505, in a state where the target substance 504 combined with the marker substance is bonded by the capturing substance. On the other hand, a detection system for the scattered light is constituted of a condenser lens 508, an interference filter 509, and a photodetector 510. The condenser lens 508 is so positioned that the focal point thereof can condense the scattered light emitted from the rear surface of the metal fine particle of the sensor medium 505. More specifically, a light scattered from the rear surface of the metal fine particle, at the interface between the metal fine particle and the transparent substance of the sensor medium 505, is formed into a parallel light beam by the condenser lens 508 and enters the interference filter 509.

The interference filter 509 is so-called Fabry-Perot type interference filter and capable of transmitting the light of a specified wavelength only. A spectrometer function is provided by utilizing a characteristic that the transmittable wavelength can be changed by changing the incident angle of the incident light to the surface of the Fabry-Perot type interference filter. An intensity of the light of a specified wavelength, separated by the interference filter 509, is detected by the photodetector 510. The result of measurement of the optical intensity of the thus separated specified wavelength is output as a detection signal 511. In practice, the detection signal 511 contains information of the specified wavelength λ separated by the interference filter 509 and a detected optical intensity P(λ) at such wavelength. A spectrum of the transmitted light can be obtained by plotting the wavelength λ of the information (λ, P(λ)) on the abscissa and the detected optical intensity P(λ) on the ordinate.

Since the irradiating light 506 in a parallel beam state is obliquely introduced to the surface of the metal fine particle of the sensor medium 505, the light entering the transparent substrate, other than the part of the metal fine particle, is transmitted and does not enter the condenser lens 508. On the other hand, the irradiating light 506 incident to the metal surface of the metal fine particle generates a near-field light on the metal surface. The near-field light couples with the free electron in the metal fine particle to generate a localized surface plasmon. Induced by an absorption derived from the localized surface plasmon resonance, a scattered light is generated from the metal fine particle. The scattered light has a wavelength distribution (spectrum) corresponding to the peak wavelength corresponding to the localized surface plasmon resonance.

Only the scattered light 507 emitted from the metal fine particle can enter the interference filter 509 after being formed into a parallel beam by the condenser lens 508 and can reach the subsequent detector 510. Therefore, in the detection system of the aforementioned construction, detected in principle is the scattered light 507 only, emitted from the metal fine particle.

The scattered light 507, emitted from the metal fine particle, is a scattered light dependent on the localized surface plasmon resonance in the metal fine particle. The scattered light dependent on the localized surface plasmon resonance exhibits a wavelength distribution (spectrum) dependent on a local change in the refractive index by the molecule immobilized on the metal fine particle. More specifically, the scattered light component dependent on the localized surface plasmon resonance has different peak wavelengths in a state where the capturing substance is bonded to the surface of the metal fine particle and in a state where the target substance is bonded to the capturing substance. Also the scattered light component dependent on the localized surface plasmon resonance has different peak wavelengths in a state where the target substance is bonded to the capturing substance and in a state where the target substance 504, combined with the marker substance, is bonded to the capturing substance. Taking the state where the capturing substance is bonded as a reference, a shift amount of the peak wavelength becomes significantly larger in the state where the target substance 504 combined with the marker substance is bonded to the capturing substance, in comparison with the state where the target substance is bonded to the capturing substance.

In an actual state, on the surface of the metal fine particle, a portion of a state bonded to the capturing substance and a portion of a state where the capturing substance is bonded with the target substance 504 combined with the marker substance are mixedly present. As a result, the scattered light component dependent on the localized surface plasmon resonance becomes a sum of a component derived from the portion of the state bonded to the capturing substance and a component derived from the portion of the state where the capturing substance is bonded with the target substance 504 combined with the marker substance. The present invention enables to observe these two components separately, utilizing the larger shift amount of the peak wavelength in the state where the target substance 504 combined with the marker substance is bonded to the capturing substance. As schematically illustrated in FIG. 4, a peak wavelength $\lambda_1$ of the component derived from the portion of the state bonded to the capturing substance and a peak wavelength $\lambda_2$ of the component derived from the portion of the state where the capturing substance is bonded with the target substance 504 combined with the marker substance are separated from each other. In such state, the ratio of the optical intensity $P(\lambda_2)$ of the scattered light component observed at the wavelength $\lambda_2$ and the optical intensity $P(\lambda_1)$ of the scattered light component observed at the wavelength $\lambda_1$ reflects a proportion of the portion of the state where the target substance 504, combined with the marker substance, is bonded to the capturing substance.

Figure 5:
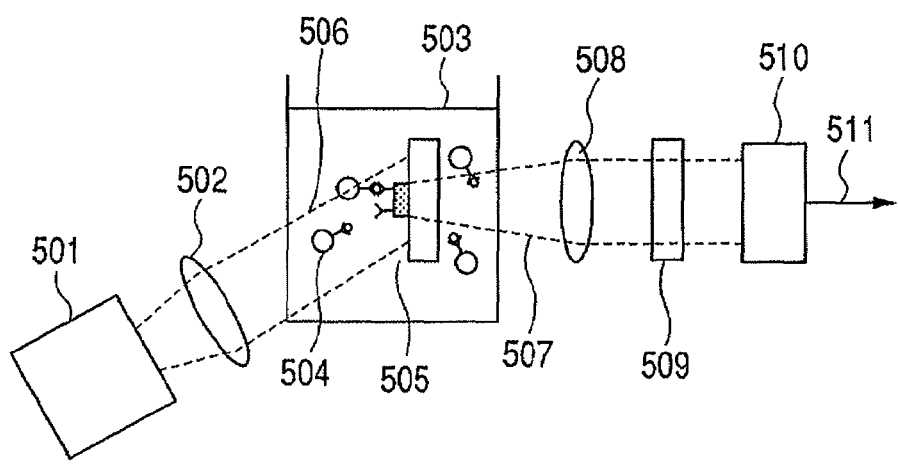
FIG. 5 is a view schematically illustrating the construction of a second exemplary embodiment of the chemical sensing apparatus of the present invention.

In the construction illustrated in FIG. 5, the scattered light 507 alone, emitted from the metal fine particle, can be detected in principle by the use of the interference filter 509. The spectrum of the scattered light may also be measured in a construction utilizing a spectrometer, instead of the interference filter 509, in such an arrangement of detecting a parallel light beam only.

Third Exemplary Embodiment

In the following, a third exemplary embodiment of the chemical sensing apparatus of the present invention will be described with reference to FIG. 6. In the present exemplary embodiment, a sensor medium 605 has such a construction that small apertures are provided in an array in a metal thin film provided on the surface of a transparent substrate, or a construction that metal fine particles are adhered in an array on the surface of a transparent substrate. The small apertures or the metal fine particles are arranged in a one-dimensional or two-dimensional array with a regular pitch.

A capturing substance, having a bonding ability to a target substance is bonded to the vicinity of the small apertures, provided in an array on the metal thin film. Otherwise, a capturing substance, having a bonding ability to a target substance is bonded to the surface of the metal fine particles, provided in an array on the surface of a transparent substrate.

Figure 6:
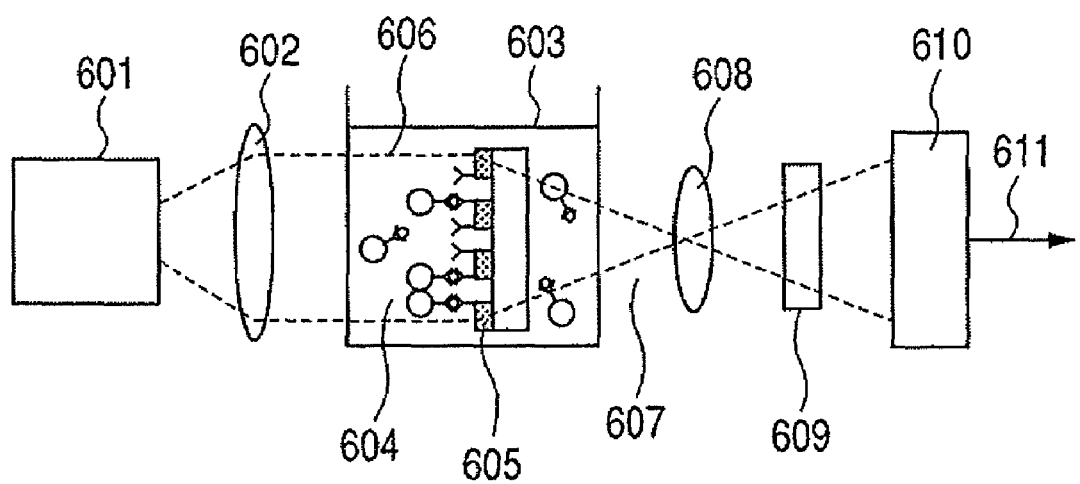
FIG. 6 is a view schematically illustrating the construction of a third exemplary embodiment of the chemical sensing apparatus of the present invention.

In the construction illustrated in FIG. 6, a tungsten lamp, a light-emitting diode or the like is utilized as a light source 601. An irradiating light 606 (having a wavelength $\lambda$ within a range of from 500 to 1,300 nm) emitted from the light source 601 irradiates a sensor medium 605 through a collimating lens 602. In the embodiment in which the small apertures are formed in an array in the metal thin film, the irradiating light 606 in a parallel beam state is introduced vertically to the upper surface of the metal thin film of the sensor medium 605 as in the first embodiment. In the embodiment in which the metal fine particles are formed in an array, the irradiating light 606 in a parallel beam state is introduced obliquely to the surface of the metal fine particle array of the sensor medium 605 as in the second embodiment.

On the other hand, a detection system for the transmitted light (or scattered light) 607 is constituted of an imaging lens 608, an interference filter 609, and an optical image sensor 610. The imaging lens 608 is so positioned as to focus an image of the transmitted lights from the small apertures formed in an array on the sensor medium 605, onto the optical image sensor 610. Otherwise, the imaging lens 608 is so positioned as to focus an image of the scattered lights from the metal fine particles arranged in an array on the sensor medium 605, onto the image sensor 610.

In the image, focused on the image sensor 610, of the transmitted lights from the small apertures formed in an array, a two-dimensional distribution of the light intensity of a specified wavelength component transmitted by the interference filter 609 is measured. The result of measurement of the two-dimensional distribution of the optical intensity of the thus separated specified wavelength component is output as a image signal 611. In practice, the image signal 611 contains two-dimensional distribution information of the specified wavelength $\lambda$ separated by the interference filter 609 and a detected optical intensity $P(\lambda)$ at such wavelength. A spectrum of the transmitted light at each small aperture (x, y) can be obtained by plotting, for each aperture (x, y), the wavelength $\lambda$ on the abscissa and of the detected light intensity $P(\lambda, s, y))$ on the ordinate.

Also in the scattered lights, focused on the image sensor 610 by the imaging lens 608, from the metal fine particles arranged in an array, a two-dimensional distribution of the light intensity of a specified wavelength component transmitted by the interference filter 609 is measured. The result of measurement of the two-dimensional distribution of the optical intensity of the thus separated specified wavelength component is output as a image signal 611.

As the optical image sensor 610, a two-dimensional image sensor such as a CCD image sensor or a CMOS image sensor can be employed advantageously.

For example in the metal fine particles arranged in an array, in the case that the target substances 604, combined with the marker substance, bonded and immobilized by the capturing substances provided on the surface of the metal fine particles have difference in the density, the spectrum of the scattered light becomes different by such difference. As schematically illustrated in FIGS. 8A and 8B, The proportion, of the component of the peak wavelength $\lambda_1$ derived from the state bonded to the capturing substance and the peak wavelength $\lambda_2$ of the component derived from the state where the capturing substance is bonded with the target substance 604 combined with the marker substance, becomes different.

Figure 7:
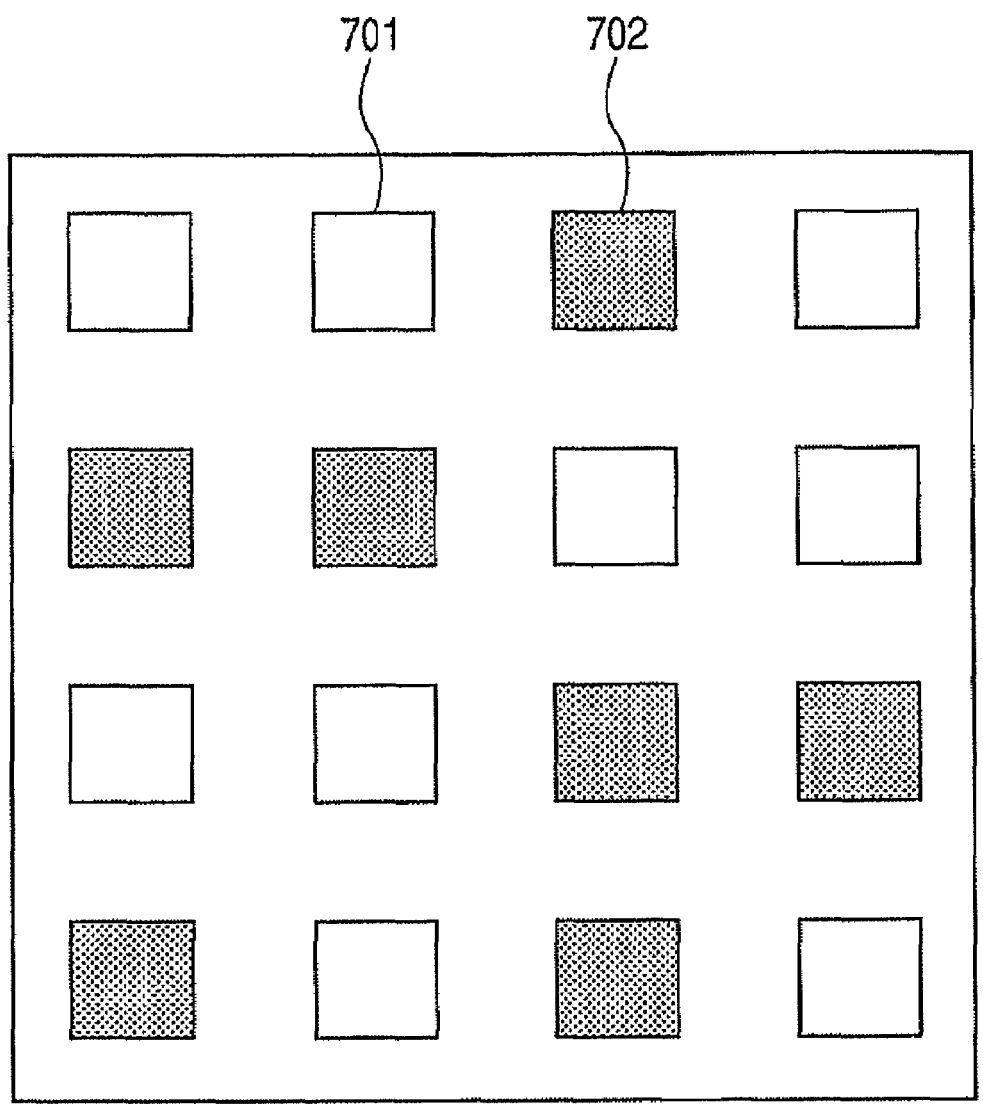
FIG. 7 is a view schematically illustrating a result, in which, in transmitted lights (or scattered lights) in matrix-arranged sensing portions, shifts in peak wavelength as illustrated in FIG. 4 are measured by an optical image sensor and are output in the form of an image signal.
Figure 8A:
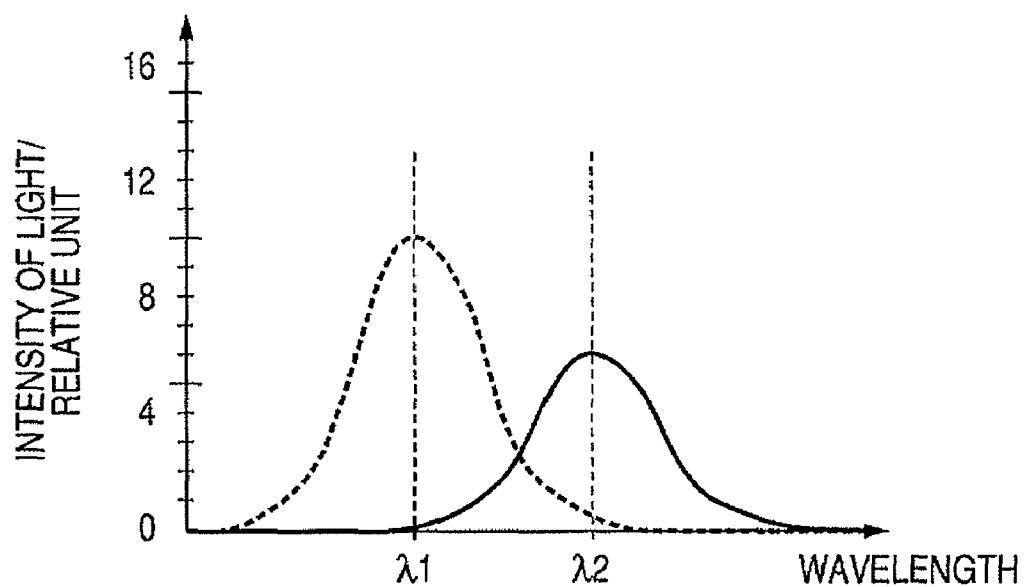
FIGS. 8A and 8B are views schematically illustrating, in the third embodiment of the chemical sensing apparatus of the present invention, a ratio of components exhibiting two peak wavelengths and constituting the spectrum of transmitted lights (or scattered lights) from plural small apertures (plural metal fine particles), and also illustrating, on the ratio of the components exhibiting two peak wavelengths, a mode of change resulting from a ratio of substance adsorption to the surface of the plural small apertures (or plural metal fine particles).
Figure 8B:
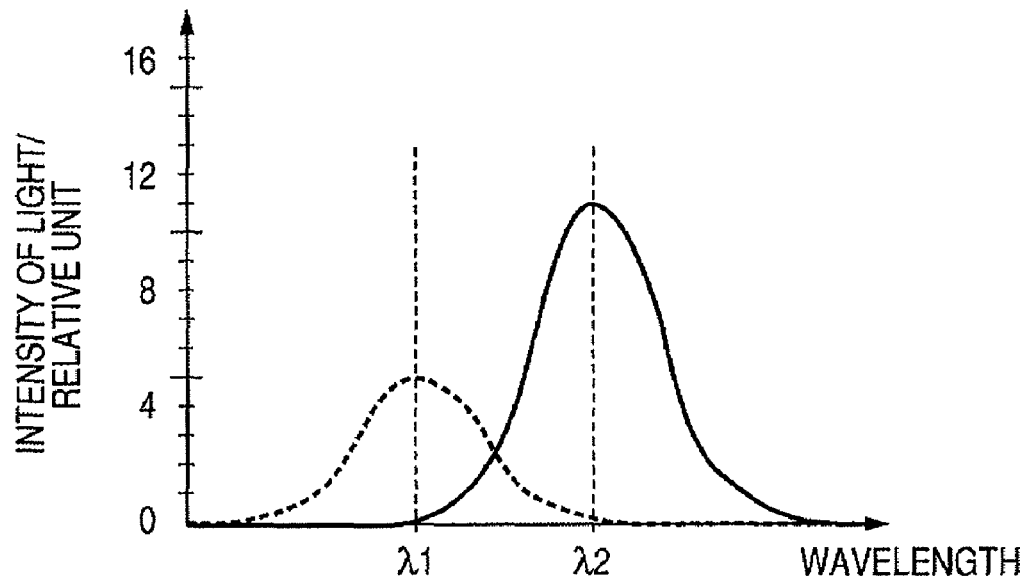

For example in the case of a difference in the scattered light spectrum (or transmitted light spectrum) as illustrated in FIGS. 8A and 8B, the state derived from the state where the capturing substance is bonded and the state derived from the where the target substance 604, combined with the marker substance, is bonded to the capturing substance are plotted two-dimensionally. In a two-dimensional plotting illustrated in FIG. 7, a metal fine particle portion, where the target substance 604 combined with the marker substance is bonded at a high density to the capturing substance on the metal fine particle, is identified as an area where the peak wavelength $\lambda_1$ has a lower intensity. On the other hand, a metal fine particle portion, where the target substance 604 combined with the marker substance is bonded only at a low density, is identified as an area where the peak wavelength $\lambda_1$ has a higher intensity. Furthermore, a metal fine particle portion, where the target substance 604 combined with the marker substance is bonded at a high density to the capturing substance on the metal fine particle, is identified as an area where the peak wavelength $\lambda_2$ has a higher intensity.

Also in the case, as illustrated in FIGS. 8A and 8B, that the component of peak wavelength $\lambda_1$ and the component of peak wavelength $\lambda_2$ have a sufficiently large shift amount in the peak wavelength, a single-pixel photodetector may be employed instead of the optical image sensor 610. The transmitted lights from 16 small apertures are focused by the imaging lens 608, and a component transmitted by the interference filter 609 is measured by a single-pixel photodetector to observe a sum of the optical intensity $\int P(\lambda, x, y)dxdy$ of the wavelength component $\lambda$.

As an example, let us consider a case where the target substance 604 combined with the marker substance is bonded only at a low density in 10 small apertures among 16 small apertures, a two-dimensional distribution of a peak wavelength component $\lambda_1$, as illustrated in FIG. 7. In such case, in the sum of the optical intensity $\int P(\lambda, x, y)dxdy$ of the wavelength component $\lambda$, a component having a peak wavelength $\lambda_1$ constitutes a principal peak, as illustrated in FIG. 8A. Also considered is a case where the target substance 604 combined with the marker substance is bonded only at a low density in 5 small apertures among 16 small apertures. In such case, in the sum of the optical intensity $\int P(\lambda, x, y)dxdy$ of the wavelength component $\lambda$, a component having a peak wavelength $\lambda_1$ is only a sub peak, as illustrated in FIG. 8B. It is thus possible to estimate, by measuring $\int P(\lambda, x, y)dxdy$ with a single-pixel photodetector, the proportion of the small apertures in which the target substance 604 combined with the marker substance is bonded only at a low density, among 16 small apertures. For example, a measurement of $\int P(\lambda, x, y)dxdy$ at the peak wavelength $\lambda_1$ enables to detect the proportion of the small apertures in which the target substance 604 combined with the marker substance is bonded only at a low density, in 16 levels of from 0/16 to 16/16.

As an example, let us assume a case in which, in the metal fine particles arranged in an array, capturing substances capable of selectively bonding different target substances are bonded. It is also assumed that, in each metal fine particle, in a state where the target substance 604 combined with the marker substance is not bonded to the capturing substance, the scattered light component exhibits a peak wavelength: $\lambda_{1-k}$ (k=1, . . . , 16). It is further assumed that, in each metal fine particle, in a state where the target substance 604 combined with the marker substance is bonded to the capturing substance, the scattered light component exhibits a peak wavelength: $\lambda_{2-k}$ (k=1, . . . , 16). In such state, the combination of the capturing substance 1-k and the target substance 604-k combined with the marker substance is so selected that the peak wavelength $\lambda_{1-k}$ (k=1, . . . , 16) satisfies peak wavelength: $\lambda_{1-k} \cong \lambda_1$ and that the peak wavelength $\lambda_{2-k}$ (k=1, . . . , 16) satisfies peak wavelength: $\lambda_{2-k} \cong \lambda_2$. When these conditions are satisfied, it is possible to simultaneously detect the plural target substances 604-k combined with the marker substance, contained in the specimen solution 603. More specifically, the scattered light components from the metal fine particles arranged in an array are detected, at wavelengths $\lambda_1$ and $\lambda_2$, as a one-dimensional or two-dimensional image. It is possible to judge, based on the results of these two measurements, presence/absence of bonding of the target substance 604-k combined with the marker substance, in each of the metal fine particles arranged in an array, by the corresponding capturing substance 1-k. Such simultaneous detecting method for plural target substances may be applied, for example, to a multi-item diagnosis in the medical diagnosis.

Fourth Exemplary Embodiment

Figure 9:
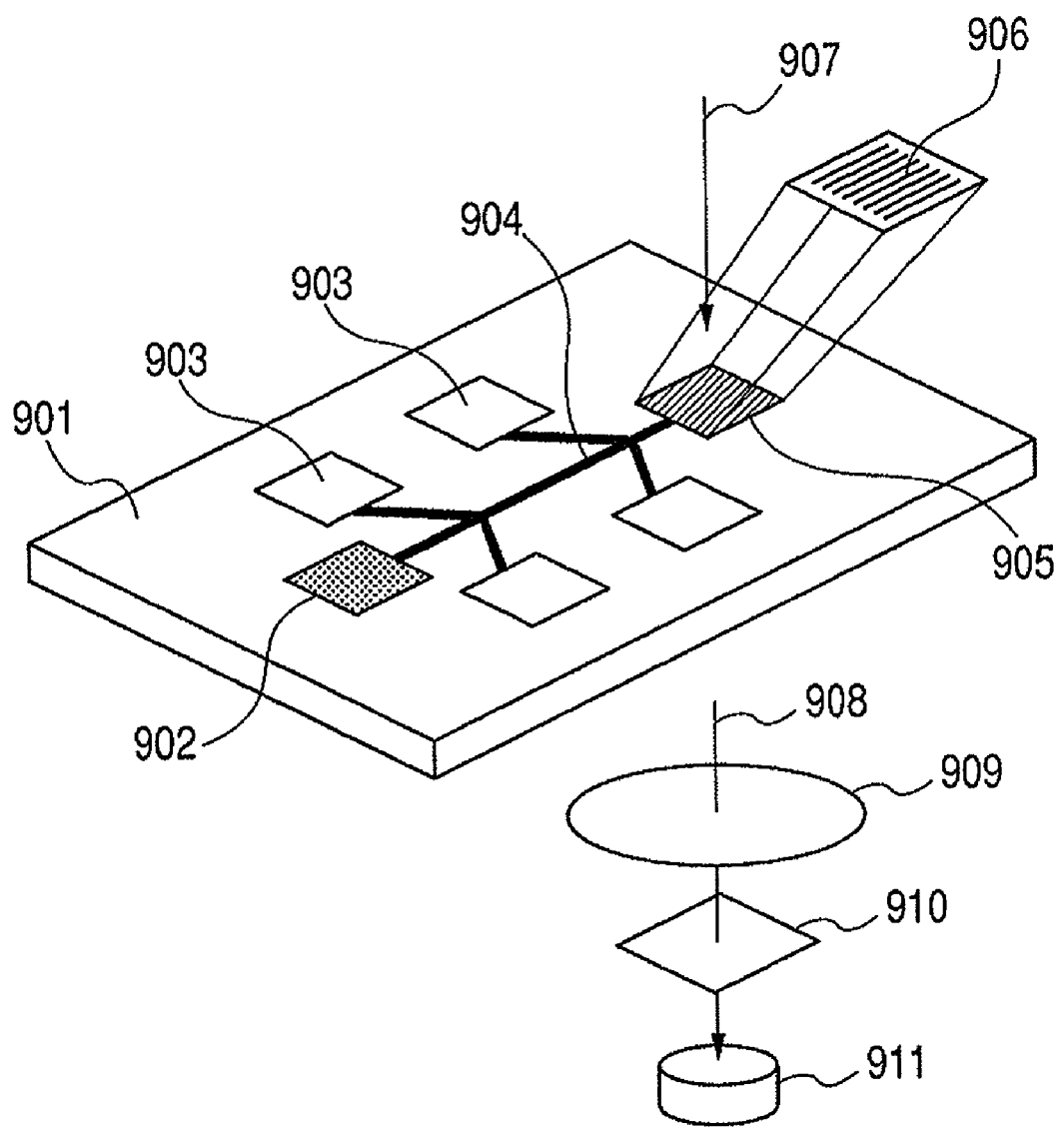
FIG. 9 is a view schematically illustrating an example of system construction in which the chemical sensing apparatus of the present invention is utilized as a detection unit in a chemical microanalytical system.

FIG. 9 illustrates an example of system construction in which the chemical sensing apparatus of the present invention is utilized as a detection unit in a chemical microanalytical system (also called μ-TAS (Micro Total Analysis System) or a Lab-on-a-chip).

In a system configuration of a chemical microanalytical system 901 as illustrated in FIG. 9, an inspected liquid injected from a sample solution injecting portion 902 passes a flow path 904, and, after reacting with a reaction solution injected from a reaction solution injecting portion 903, reaches a detecting portion 905. In the chemical microanalytical system 901 itself, the detecting portion 905 is formed on a transparent substrate constituted of a translucent material. In the detecting portion 905, as illustrated in a magnified manner, a metal thin film having small apertures 906 arranged in a one-dimensional array is adhered to a bottom surface of a liquid reservoir structure provided in the transparent substrate. In the small apertures 906 formed in a one-dimensional array in the metal thin film, each small aperture has a size smaller than the wavelength of an irradiating light 907. Also in the vicinity of each small aperture 906 formed in the metal thin film, a capturing substance, capable of selectively bonding with the target substance to be detected, is bonded on the surface of the metal thin film. Also the specimen solution guided to the detecting portion 904 contains the target substance in the form of a target substance combined with a marker substance.

After the inspected liquid is subjected for example to the aforementioned reaction, a second capturing substance combined with a marker substance is reacted with the target substance to cause a bonding of the second capturing substance and the target substance thereby obtaining the target substance combined with the marker substance. Otherwise, the aforementioned reaction itself, applied to the inspected liquid, may be a reaction of a second capturing substance combined with a marker substance with the target substance to cause a bonding of the second capturing substance and the target substance thereby obtaining the target substance combined with the marker substance.

The inspected liquid, upon reaching the detecting portion 905, sinks into the detecting portion 905 and covers the surface of the metal thin film, having the small apertures 906. As a result, the target substance combined with the marker substance, contained in the inspected liquid, becomes bonded by the capturing substance bonded in the vicinity of the small aperture 906.

On the other hand, the chemical sensing apparatus utilized as the detecting unit adopts a construction in which the irradiating light 907, formed as a parallel beam, is introduced to the detecting portion 905, vertically to the surface of the metal thin film having the small apertures 906. A transmitted light 908, transmitted by the small apertures 906 arranged in an array in the metal thin film under the vertical incident condition, is focused by a lens 909 onto an interference filter 910. A transmitted light component, passed by the interference filter 910, is detected by a photomultiplier 911. Thus, it corresponds, in the aforementioned third exemplary embodiment, to an embodiment employing a single-pixel photodetector instead of the optical image sensor. The lights transmitted by the small apertures in a one-dimensional array are focused by an imaging lens 909, and the transmitted light component of a wavelength $\lambda$, transmitted by the interference filter 910, is observed by the photomultiplier 911 as the sum of the optical intensity $\int P(\lambda, x, y)dxdy$ of the wavelength component $\lambda$.

Fifth Exemplary Embodiment

Figure 10:
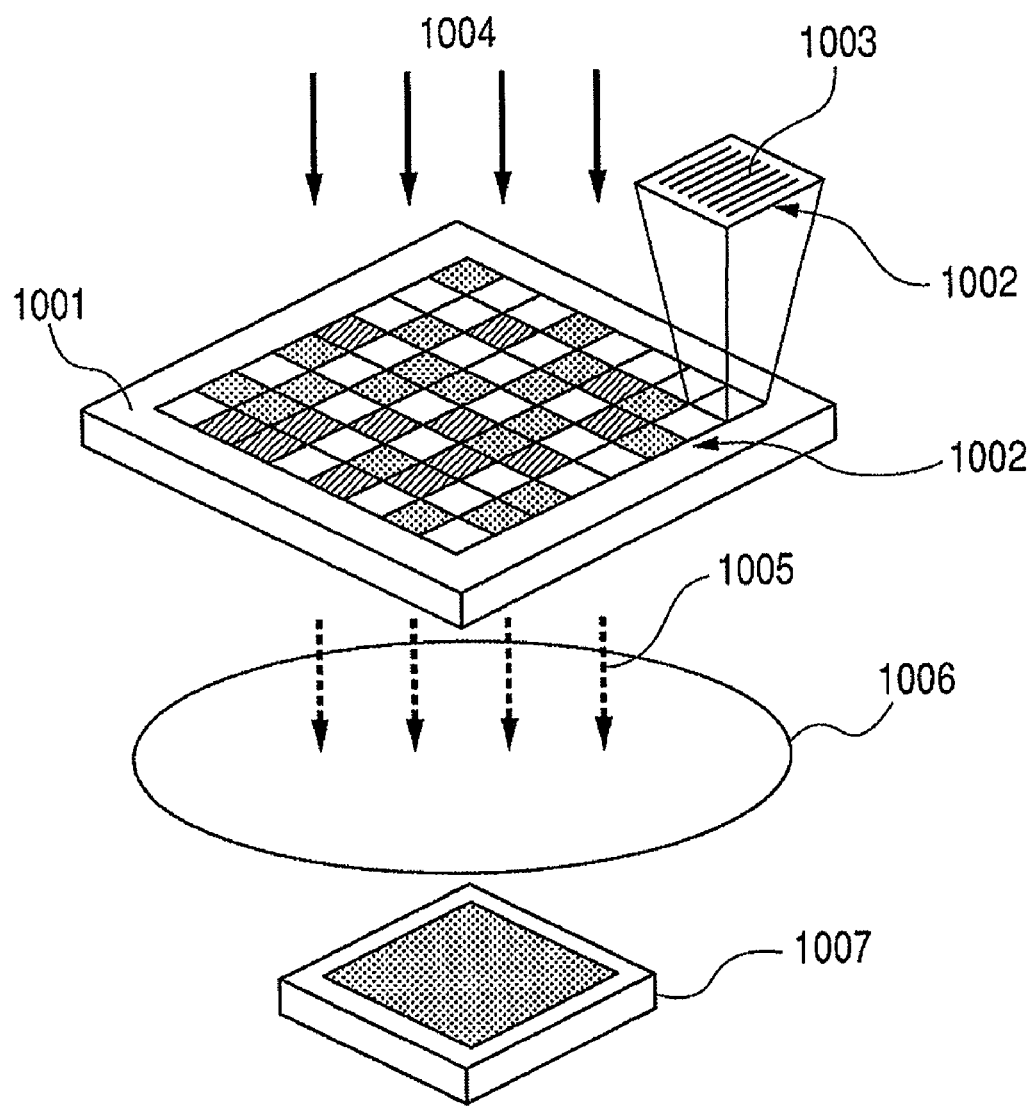
FIG. 10 is a view schematically illustrating an example of system construction in which the chemical sensing apparatus of the present invention is utilized, in a target substance detection system utilizing a DNA chip or a protein chip, for detecting presence/absence of immobilization of the target substance on a detection cell disposed on such chip.

FIG. 10 illustrates an example of the system construction in which the chemical sensing apparatus of the present invention is utilized as detecting means in each detection cell of a DNA chip or a protein chip.

A DNA chip/protein chip 1001 illustrated in FIG. 10 has a construction that plural cells are arranged in a two-dimensional array. Each detection cell 1002 is prepared with a transparent substrate, constituted of a translucent material. A metal thin film, having small apertures 1003 arranged in a one-dimensional array, is adhered on a bottom surface of each detection cell 1002. In the small apertures 1003 arranged in a one-dimensional array in the metal thin film, each small aperture has a size smaller than the wavelength of an irradiating light 1004. Also in case of a DNA chip, in the vicinity of each small aperture 1003 formed in the metal thin film, a DNA probe is bonded, as a capturing substance, on the surface of the metal thin film. Also in case of a protein chip, in the vicinity of each small aperture 1003 formed in the metal thin film, a specific antibody to a protein to be detected (target substance) is bonded, as a capturing substance, on the surface of the metal thin film.

In case of the DNA chip, as a target substance combined with a marker substance to be bonded with the DNA probe as the capturing substance, for example a nucleic acid molecule, which is combined at the 5'-terminal with the marker substance across a linker, is contained in the specimen solution. Also in case of the protein chip, for example a second capturing substance combined with a marker substance is reacted with the target substance to combine the second capturing substance with the target substance, thereby obtaining the target substance combined with the marker substance.

In such case, it is assumed that, in each detection cell 1002, in a state where the target substance combined with the marker substance is not bonded to the capturing substance, the transmitted light component through the small aperture exhibits a peak wavelength: $\lambda_{1-k}$ (k=1, ..., N). It is further assumed that, in each detection cell, in a state where the target substance combined with the marker substance is bonded to the capturing substance, the transmitted light component through the small aperture exhibits a peak wavelength: $\lambda_{2-k}$ (k=1, ..., N). In such state, the combination of the capturing substance and the target substance combined with the marker substance is so selected that the peak wavelength $\lambda_{1-k}$ (k=1, ..., N) satisfies peak wavelength: $\lambda_{1-k} \cong \lambda_1$ and that the peak wavelength $\lambda_{2-k}$ (k=1, ..., N) satisfies peak wavelength: $\lambda_{2-k} \cong \lambda_2$. When these conditions are satisfied, it is possible, utilizing the DNA chip/protein chip 1001, to simultaneously detect presence/absence of bonding of the target substance combined with the marker substance, in each detection cell 1002.

In this case, the chemical sensing apparatus utilized as the detecting unit adopts a construction in which the irradiating light 1004, formed as a parallel beam, is introduced to each detecting cell 1002 of the DNA chip/protein chip 1001, vertically to the surface of the metal thin film having the small apertures 1003. A transmitted light 1005, transmitted by the small apertures 1003 arranged in an array in the metal thin film under the vertical incident condition, is focused by a lens 1006 onto an interference filter. A transmitted light component, passed by the interference filter, is detected by a CCD camera 1007. Thus, it corresponds, in the aforementioned third exemplary embodiment, to a construction in which the image of the transmitted light from the small apertures in an array is focused by an imaging lens onto an interference filter and a two-dimensional distribution of optical intensity of the component of wavelength $\lambda$ passed by the interference filter is measured. Based on the two-dimensional distribution $P(\lambda, x, y)$ of the optical intensity of the component of wavelength $\lambda$ detected by the CCD camera 1007, the sum of the optical intensity $\int P(\lambda, x, y)dxdy$ of the wavelength component $\lambda$ is calculated for each detection cell 1002. A pattern information indicating the detection result for the entire DNA chip/protein chip 1001 can be obtained by two-dimensionally plotting the results of such calculation, in correspondence to the arrangement of each detection cell 1002 in the DNA chip/protein chip 1001.

In the construction of FIG. 10, in which the irradiating light 1004 in a parallel beam is vertically introduced to the surface of the metal thin film, a part of the parallel incident light can pass through the metal thin film in a region where the small apertures are not formed. Such transmitted light, directly transmitted by the metal thin film, is substantially eliminated by constructing the detection system for the transmitted (or scattered) light by an imaging lens, an interference filter and an optical image sensor, as described in the third exemplary embodiment.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-325949, filed Dec. 1, 2006, and No. 2007-294265 filed on Nov. 13, 2007 which are hereby incorporated by reference herein in their entirety.

What is claimed is:

1. A chemical sensing apparatus for detecting a target substance by immobilizing the target substance combined with a marker substance through a bond with a capturing substance, comprising:
   a light source;
   a metal thin film having an aperture smaller than a wavelength of a light emitted from the light source, or a metal fine particle smaller than the wavelength;
   a substrate bearing the metal thin film or the metal fine particle on the surface of the substrate;
   the capturing substance, bonded to a surface of the metal thin film or to a surface of the metal fine particle; and
   a photodetector for detecting light emitted from the light source through the aperture or scattered light emitted from the metal fine particle when irradiating the metal thin film or the metal fine particle with the light emitted from the light source,
   wherein the marker substance has a size from 1/10 times to 10 times that of the aperture or that of the metal fine particle.

2. A chemical sensing apparatus according to claim 1, wherein the marker substance is a dielectric fine particle.

3. A chemical sensing apparatus according to claim 1, wherein the marker substance is a second metal fine particle.

4. A chemical sensing apparatus according to claim 1, wherein the marker substance is a magnetic fine particle.

5. A chemical sensing apparatus according to claim 1, wherein the photodetector has a function capable of detecting a spectral shape of the transmitted light through the aperture formed in the metal thin film, or the scattered light emitted from the metal fine particle.

6. A chemical sensing apparatus according to claim 1, wherein plural such apertures in the metal thin film or plural such metal fine particles are provided, and the plural apertures or the plural metal fine particles are arranged in a one-dimensional or two-dimensional array on the surface of the substrate.

7. A chemical sensing apparatus according to claim 6, wherein the photodetector has a function capable of detecting the transmitted light through the plural apertures or the scattered light emitted from the plural metal fine particles, arranged in the one-dimensional or two-dimensional array on the surface of the transparent substrate, as one-dimensional or two-dimensional image information.

8. A chemical sensing apparatus according to claim 1, wherein the irradiating method of the light from the light source and the arrangement of the photodetector are in an dark field illumination arrangement, in which, when the light from the light source irradiates the metal thin film having the aperture or the metal fine particle, the transmitted light through the aperture formed in the metal thin film or the scattered light from the metal fine particle alone is detected by the photodetector.

9. A chemical sensing apparatus according to claim 1, comprising a system construction wherein the chemical sensing apparatus is incorporated in a chemical microanalytical system, as a detection unit in a detection portion of the chemical microanalytical system.

10. A chemical sensing apparatus according to claim 1, comprising a system construction wherein the chemical sensing apparatus is incorporated in a target substance detecting system utilizing a DNA chip, as a detection unit in a detection portion of the target substance detecting system utilizing a DNA chip.

11. A chemical sensing apparatus according to claim 1, comprising a system construction wherein the chemical sensing apparatus is incorporated in a target substance detecting system utilizing a protein chip, as a detection unit in a detection portion of the target substance detecting system utilizing a protein chip.

12. A chemical sensing method for detecting a target substance in a specimen by immobilizing the target substance combined with a marker substance through a bond with a capturing substance, the method comprising the steps of:
   (A) preparing a chemical sensing apparatus comprising
      a light source,
      a metal thin film having an aperture smaller than a wavelength of a light emitted from the light source, or a metal fine particle smaller than the wavelength,
      a substrate bearing the metal thin film or the metal fine particle on the surface of the substrate,
      the capturing substance, bonded to a surface of the metal thin film or to a surface of the metal fine particle, and
      a photodetector for detecting light emitted from the light source through the aperture or the metal fine particle,
      wherein the marker substance to be combined with the target substance has from 1/10 times to 10 times the size of the aperture or of the metal fine particle;
   (B) combining the target substance in the specimen with the marker substance;
   (C) bringing the specimen into contact with the metal thin film or the metal fine particle of the chemical sensing apparatus;
   (D) irradiating the metal thin film or the metal fine particle with light emitted from the light source after the bringing-into-contact step, and
   (E) detecting light emitted from the light source through the aperture of the metal thin film or the metal fine particle by means of the photodetector.

13. A chemical sensing method according to claim 12, wherein
   the photodetector has a function capable of detecting a spectral shape of the transmitted light through the aperture formed in the metal thin film, or the scattered light emitted from the metal fine particle, and
   in detecting the transmitted light transmitted by the aperture formed in the metal thin film or the scattered light emitted from the metal fine particle by the photodetector, detects a spectral shape of the transmitted light through the aperture formed in the metal thin film, or the scattered light emitted from the metal fine particle.

14. A chemical sensing method according to claim 12, wherein the photodetector has a function of detecting the light from a one-dimensionally or two-dimensionally spreading measurement area, as one-dimensional or two-dimensional image information, and
   in detecting the transmitted light through the aperture formed in the metal thin film or the scattered light from the metal fine particle, detects the light from an area irradiated with the light from the light source, as one-dimensional or two-dimensional image information.

15. A chemical sensing method according to claim 12, further comprising, in detecting the transmitted light through the aperture formed in the metal thin film or the scattered light from the metal fine particle by the photodetector, an operation of calculating a gradation of a light intensity, based on the result of measurement of the light intensity detected by the photodetector.

16. A chemical sensing method according to claim 12, wherein the capturing substance, bonded to the metal surface of the metal thin film in the vicinity of the aperture or to the surface of the metal fine particle, is bonded to the metal surface by irradiating the metal surface of the metal thin film in the vicinity of the aperture or the surface of the metal fine particle with a second light to induce a photochemical reaction that is used for bonding the capturing substance to the metal surface.

* * * * *